United States Patent
Flatland et al.

(10) Patent No.: US 8,529,467 B2
(45) Date of Patent: *Sep. 10, 2013

(54) TISSUE EXCISION DEVICE WITH A COLLAPSIBLE STYLET

(75) Inventors: Martin L. Flatland, Kalamazoo, MI (US); Bamdad Hassanpourgol, McAllen, TX (US)

(73) Assignee: Siteselect Medical Technologies, Inc., McAllen, TX (US)

( * ) Notice: Subject to any disclaimer, the term of this patent is extended or adjusted under 35 U.S.C. 154(b) by 288 days.

This patent is subject to a terminal disclaimer.

(21) Appl. No.: 13/074,746

(22) Filed: Mar. 29, 2011

(65) Prior Publication Data

US 2011/0245725 A1    Oct. 6, 2011

Related U.S. Application Data

(60) Provisional application No. 61/319,159, filed on Mar. 30, 2010, provisional application No. 61/319,160, filed on Mar. 30, 2010, provisional application No. 61/319,162, filed on Mar. 30, 2010, provisional application No. 61/319,155, filed on Mar. 30, 2010, provisional application No. 61/319,148, filed on Mar. 30, 2010, provisional application No. 61/319,157, filed on Mar. 30, 2010, provisional application No. 61/319,209, filed on Mar. 30, 2010, provisional application No. 61/319,210, filed on Mar. 30, 2010, provisional application No. 61/319,217, filed on Mar. 30, 2010, provisional application No. 61/319,218, filed on Mar. 30, 2010, provisional application No. 61/319,223, filed on Mar. 30, 2010, provisional application No. 61/319,528, filed on Mar. 31, 2010, provisional application No. 61/324,172, filed on Apr. 14, 2010.

(51) Int. Cl.
*A61B 10/00* (2006.01)
(52) U.S. Cl.
USPC ........................................... 600/564
(58) Field of Classification Search
USPC ................................ 600/562–568
See application file for complete search history.

(56) References Cited

U.S. PATENT DOCUMENTS 4,461,305 A    7/1984   Cibley
4,616,656 A   10/1986   Nicholson et al.

(Continued)

FOREIGN PATENT DOCUMENTS

AU    199739940 B2    4/1998
AU    199893743 B2    4/1999

(Continued)

OTHER PUBLICATIONS

Flatland et al., "Tissue Excision Device With a Retractable Back Hook" (U.S. Appl. No. 13/074,716), filed Mar. 29, 2011.

(Continued)

*Primary Examiner* — Brian Szmal
(74) *Attorney, Agent, or Firm* — Howard & Howard Attorneys PLLC

(57) ABSTRACT

A biopsy device includes a coring cannula, a retract stylet, and a localization needle. The coring cannula has a longitudinal axis and a shaft centered on the axis. The stylet has a tip containing at least one blade and a central passage. The localization needle has a channel and is slidably disposed within the central passage. A drive mechanism rotates the cannula and moves the cannula in a direction parallel to the longitudinal axis of the cannula. A guide element has a first end and a second end and is slidably disposed within the channel of the localization needle. The guide element is movable from a first position to a second position within the localization needle.

18 Claims, 34 Drawing Sheets

(56) References Cited

U.S. PATENT DOCUMENTS

| | | |
|---|---|---|
| 4,790,329 A | 12/1988 | Simon |
| 4,986,279 A | 1/1991 | O'Neill |
| 5,030,201 A | 7/1991 | Palestrant |
| 5,060,658 A | 10/1991 | Dejter, Jr. et al. |
| 5,069,679 A | 12/1991 | Taheri |
| 5,111,828 A | 5/1992 | Kornberg et al. |
| 5,197,482 A | 3/1993 | Rank et al. |
| 5,197,484 A | 3/1993 | Kornberg et al. |
| 5,199,441 A | 4/1993 | Hogle |
| 5,213,100 A | 5/1993 | Summ |
| 5,353,804 A | 10/1994 | Kornberg et al. |
| 5,386,447 A | 1/1995 | Siczek |
| 5,396,897 A | 3/1995 | Jain et al. |
| 5,486,183 A | 1/1996 | Middleman et al. |
| 5,499,989 A | 3/1996 | LaBash |
| 5,609,152 A | 3/1997 | Pellegrino et al. |
| 5,647,374 A | 7/1997 | Cutrer |
| 5,782,775 A | 7/1998 | Milliman et al. |
| 5,800,457 A | 9/1998 | Gelbfish |
| 5,817,034 A | 10/1998 | Milliman et al. |
| 5,848,978 A | 12/1998 | Cecchi |
| 5,857,982 A | 1/1999 | Milliman et al. |
| 5,868,673 A | 2/1999 | Vesely |
| 5,888,196 A | 3/1999 | Bonutti |
| 5,913,857 A | 6/1999 | Ritchart et al. |
| 5,954,670 A | 9/1999 | Baker |
| 5,961,457 A | 10/1999 | Raylman et al. |
| 6,007,495 A | 12/1999 | Matula |
| 6,019,733 A | 2/2000 | Farascioni |
| 6,022,325 A | 2/2000 | Siczek et al. |
| 6,036,657 A | 3/2000 | Milliman et al. |
| 6,053,925 A | 4/2000 | Barnhart |
| 6,077,231 A | 6/2000 | Milliman et al. |
| 6,080,113 A | 6/2000 | Heneveld et al. |
| 6,080,114 A | 6/2000 | Russin |
| 6,093,154 A | 7/2000 | Burek et al. |
| 6,136,014 A | 10/2000 | Sirimanne et al. |
| 6,142,955 A | 11/2000 | Farascioni et al. |
| 6,165,137 A | 12/2000 | Milliman et al. |
| 6,176,835 B1 | 1/2001 | Pachal |
| 6,213,957 B1 | 4/2001 | Milliman et al. |
| 6,267,732 B1 | 7/2001 | Heneveld et al. |
| 6,383,145 B1 | 5/2002 | Worm et al. |
| 6,387,056 B1 | 5/2002 | Kieturakis |
| 6,432,064 B1 | 8/2002 | Hibner et al. |
| 6,436,054 B1 | 8/2002 | Viola et al. |
| 6,471,709 B1 | 10/2002 | Fawzi et al. |
| 6,485,436 B1 | 11/2002 | Truckai et al. |
| 6,488,636 B2 | 12/2002 | Bryan et al. |
| 6,512,943 B1 | 1/2003 | Kelcz |
| 6,551,253 B2 | 4/2003 | Worm et al. |
| 6,554,779 B2 | 4/2003 | Viola et al. |
| 6,623,437 B2 | 9/2003 | Hinchliffe et al. |
| 6,626,849 B2 | 9/2003 | Huitema et al. |
| 6,716,180 B2 | 4/2004 | Fontenot |
| 6,730,044 B2 | 5/2004 | Stephens et al. |
| 6,889,073 B2 | 5/2005 | Lampman et al. |
| 6,904,305 B2 | 6/2005 | Tsekos |
| 6,908,440 B2 | 6/2005 | Fisher |
| 6,918,880 B2 | 7/2005 | Brookner et al. |
| 6,976,968 B2 | 12/2005 | Ritchart et al. |
| 7,056,690 B2 | 6/2006 | Laskey et al. |
| 7,060,039 B2 | 6/2006 | Voegele |
| 7,077,842 B1 | 7/2006 | Cosman |
| 7,097,648 B1 | 8/2006 | Globerman et al. |
| 7,149,566 B2 | 12/2006 | Lee |
| 7,169,114 B2 | 1/2007 | Krause |
| 7,276,032 B2 | 10/2007 | Hibner |
| 7,309,316 B1 | 12/2007 | Flynn et al. |
| 7,329,228 B2 | 2/2008 | Burbank et al. |
| 7,379,769 B2 | 5/2008 | Piron et al. |
| 7,479,152 B2 | 1/2009 | Fulton, III et al. |
| 7,513,877 B2 | 4/2009 | Viola |
| 7,549,424 B2 | 6/2009 | Desai |
| 7,648,466 B2 | 1/2010 | Stephens et al. |
| 7,662,109 B2 | 2/2010 | Hibner |
| 7,711,407 B2 | 5/2010 | Hughes et al. |
| 7,717,861 B2 | 5/2010 | Weikel et al. |
| 2001/0020139 A1 | 9/2001 | Milliman et al. |
| 2002/0056160 A1 | 5/2002 | Falbo, Sr. et al. |
| 2002/0099264 A1 | 7/2002 | Fontenot |
| 2002/0099307 A1 | 7/2002 | Krause et al. |
| 2002/0151820 A1 | 10/2002 | Dvorak et al. |
| 2002/0156360 A1 | 10/2002 | Ihamaki et al. |
| 2003/0014093 A1 | 1/2003 | Makin |
| 2003/0073895 A1 | 4/2003 | Nields et al. |
| 2003/0181896 A1 | 9/2003 | Zvuloni et al. |
| 2003/0199785 A1 | 10/2003 | Hibner et al. |
| 2004/0097981 A1 | 5/2004 | Selis |
| 2004/0147917 A1 | 7/2004 | Mueller, Jr. et al. |
| 2004/0162505 A1 | 8/2004 | Kaplan et al. |
| 2004/0171933 A1 | 9/2004 | Stoller et al. |
| 2004/0215215 A1 | 10/2004 | McClellan et al. |
| 2004/0267121 A1 | 12/2004 | Sarvazyan et al. |
| 2005/0004453 A1 | 1/2005 | Tearney et al. |
| 2005/0209530 A1 | 9/2005 | Pflueger |
| 2006/0009712 A1 | 1/2006 | Van Bladel et al. |
| 2006/0058703 A1 | 3/2006 | Huenerbein |
| 2006/0074344 A1 | 4/2006 | Hibner |
| 2006/0100480 A1 | 5/2006 | Ewers et al. |
| 2006/0167470 A1 | 7/2006 | McGuckin |
| 2006/0184063 A1 | 8/2006 | Miller |
| 2007/0118049 A1 | 5/2007 | Viola |
| 2007/0141587 A1 | 6/2007 | Baker et al. |
| 2007/0142778 A1 | 6/2007 | Elbert et al. |
| 2007/0219459 A1 | 9/2007 | Cohen |
| 2007/0232953 A1 | 10/2007 | Dietz et al. |
| 2007/0255173 A1 | 11/2007 | Hibner |
| 2007/0282221 A1 | 12/2007 | Wang et al. |
| 2008/0045833 A1 | 2/2008 | Defreitas et al. |
| 2008/0058730 A1 | 3/2008 | Melsheimer |
| 2008/0103387 A1 | 5/2008 | Gross |
| 2008/0103411 A1 | 5/2008 | Van Bladel et al. |
| 2008/0146905 A1 | 6/2008 | Keppel et al. |
| 2008/0187095 A1 | 8/2008 | Boone et al. |
| 2008/0221478 A1 | 9/2008 | Ritchie et al. |
| 2008/0255444 A1 | 10/2008 | Li |
| 2008/0287827 A1 | 11/2008 | Sarkar et al. |
| 2009/0012423 A1 | 1/2009 | Peters |
| 2009/0048532 A1 | 2/2009 | Stephens et al. |
| 2009/0076412 A1 | 3/2009 | Rioux et al. |
| 2009/0080604 A1 | 3/2009 | Shores et al. |
| 2009/0082763 A1 | 3/2009 | Quick et al. |
| 2009/0088665 A1 | 4/2009 | Beckman et al. |
| 2009/0112085 A1 | 4/2009 | Eby |
| 2009/0131826 A1 | 5/2009 | Teague |
| 2009/0137927 A1 | 5/2009 | Miller |
| 2009/0156961 A1 | 6/2009 | Tsonton et al. |
| 2009/0163830 A1 | 6/2009 | Hibner et al. |
| 2009/0270725 A1 | 10/2009 | Leimbach et al. |
| 2010/0030107 A1 | 2/2010 | Hancock |
| 2010/0049086 A1 | 2/2010 | Hibner et al. |
| 2010/0081964 A1 | 4/2010 | Mark et al. |
| 2010/0113973 A1 | 5/2010 | Hibner et al. |
| 2010/0130887 A1 | 5/2010 | Selis |
| 2011/0245716 A1* | 10/2011 | Flatland et al. ............... 600/567 |

FOREIGN PATENT DOCUMENTS

| | | |
|---|---|---|
| CA | 2 184 973 A1 | 3/1997 |
| CA | 2 258 193 A1 | 12/1997 |
| CA | 2 214 873 A1 | 4/1998 |
| CA | 2 424 355 A1 | 4/2002 |
| CA | 2 302 158 C | 2/2009 |
| DE | 296 23 929 U1 | 9/2000 |
| EP | 0 761 170 A3 | 3/1998 |
| EP | 0 841 036 A1 | 5/1998 |
| EP | 0 858 774 A2 | 8/1998 |
| EP | 1 051 946 A2 | 11/2000 |
| EP | 1 634 543 B1 | 9/2004 |
| JP | 10-118086 | 5/1998 |

| | | |
|---|---|---|
| WO | 97/47243 A1 | 12/1997 |
| WO | 99/13775 A1 | 3/1999 |
| WO | 02/32293 A2 | 4/2002 |

OTHER PUBLICATIONS

Flatland et al., "Tissue Excision Device" (U.S. Appl. No. 13/074,726), filed Mar. 29, 2011.

Flatland et al., "Tissue Excision Device With a Flexible Transection Blade" (U.S. Appl. No. 13/074,728), filed Mar. 29, 2011.

Flatland et al., "Tissue Excision Device With a Modified Cutting Edge" (U.S. Appl. No. 13/074,732), filed Mar. 29, 2011.

Flatland et al., "Tissue Excision Device With a Reduced Diameter Cannula" (U.S. Appl. No. 13/074,738), filed Mar. 29, 2011.

Flatland et al., "Tissue Excision Device With an Independent Needle" (U.S. Appl. No. 13/074,754), filed Mar. 29, 2011.

Flatland et al., "Tissue Excision Device With a Retracting Stylet Blade" (U.S. Appl. No. 13/074,758), filed Mar. 29, 2011.

Flatland et al., "Tissue Excision Device With an Expanding Localization Needle" (U.S. Appl. No. 13/074,501), filed Mar. 29, 2011.

Flatland et al., "Tissue Excision Device" (U.S. Appl. No. 13/074,495), filed Mar. 29, 2011.

Flatland et al., "Tissue Excision Device With With Rotating Stylet Blades" (U.S. Appl. No. 13/074,505), filed Mar. 29, 2011.

Flatland et al., "Tissue Excision Device" (U.S. Appl. No. 13/074,511), filed Mar. 29, 2011.

Flatland et al., "Tissue Excision Device" (PCT International Patent No. PCT/US2011/030334), filed Mar. 29, 2011.

International Search Report and Written Opinion dated Jun. 20, 2011.

* cited by examiner

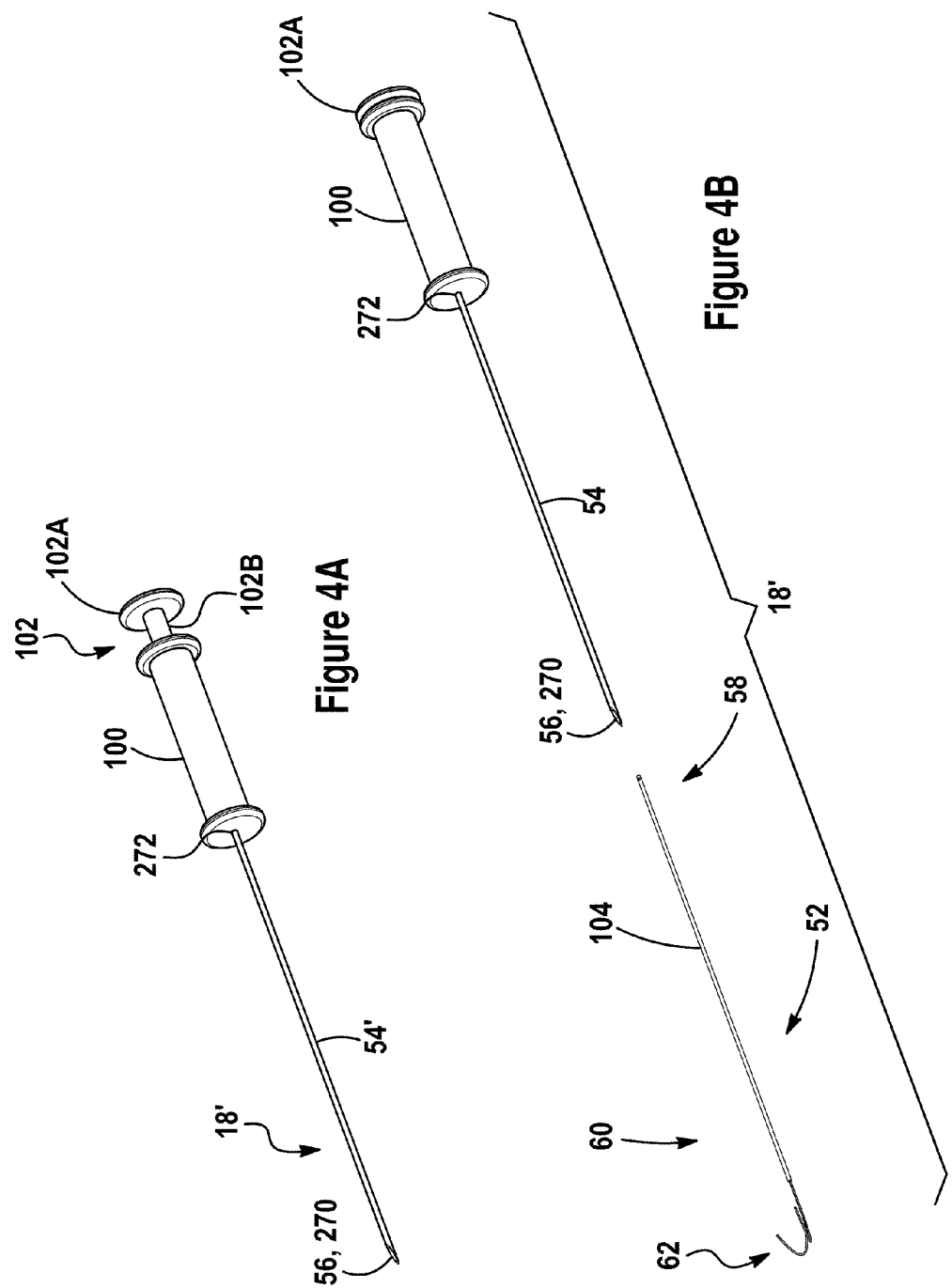

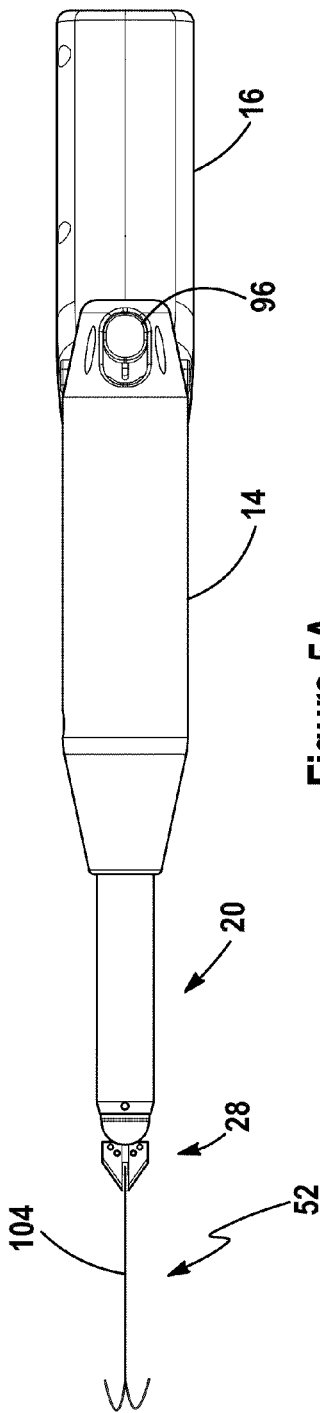
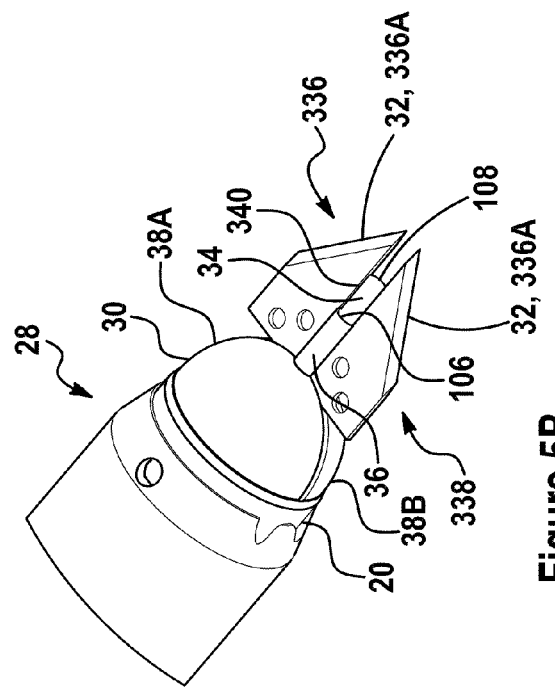
Figure 5A
Figure 5B

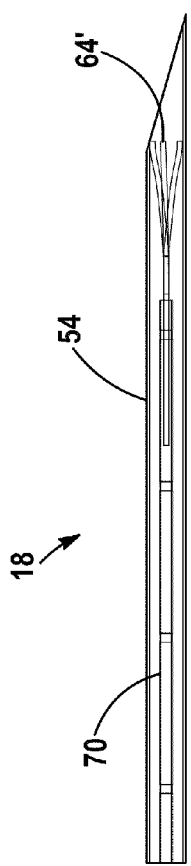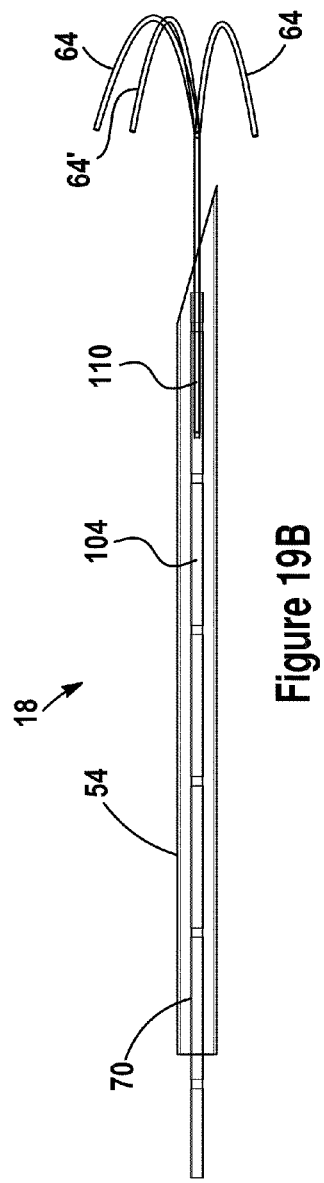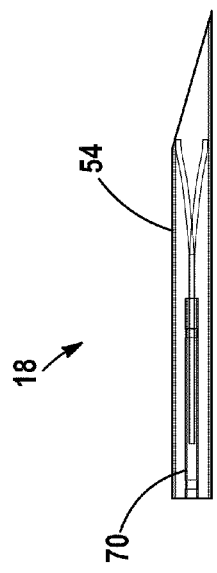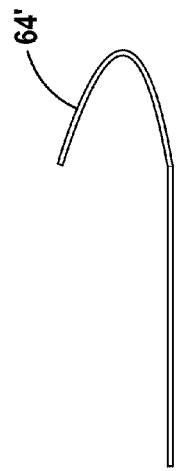
Figure 19A
Figure 19B
Figure 19C
Figure 19D

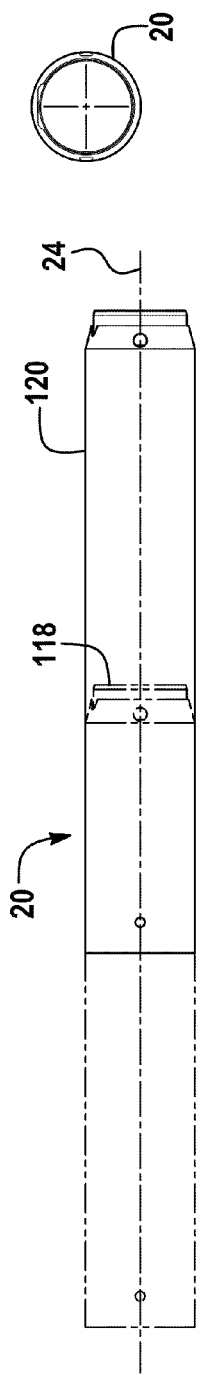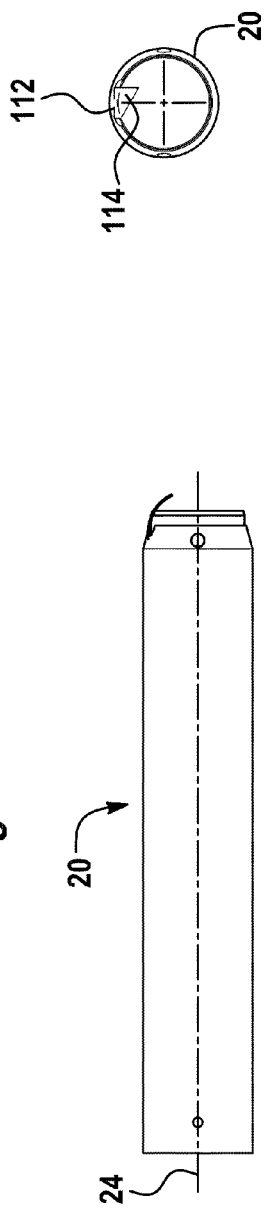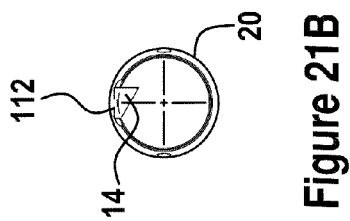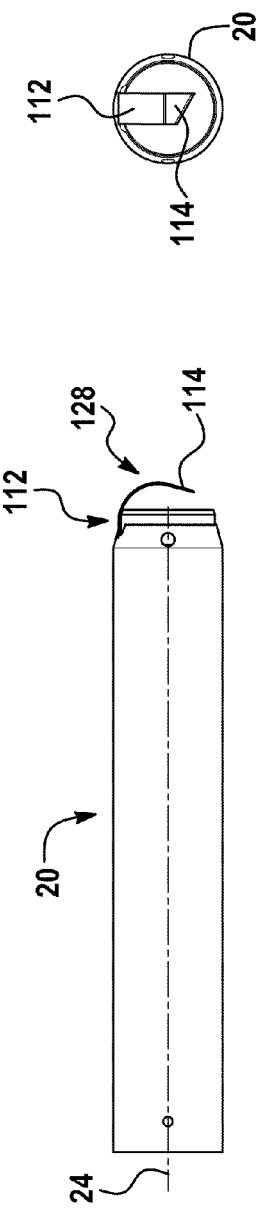
Figure 20A  Figure 20B  Figure 21A  Figure 21B  Figure 22A  Figure 22B

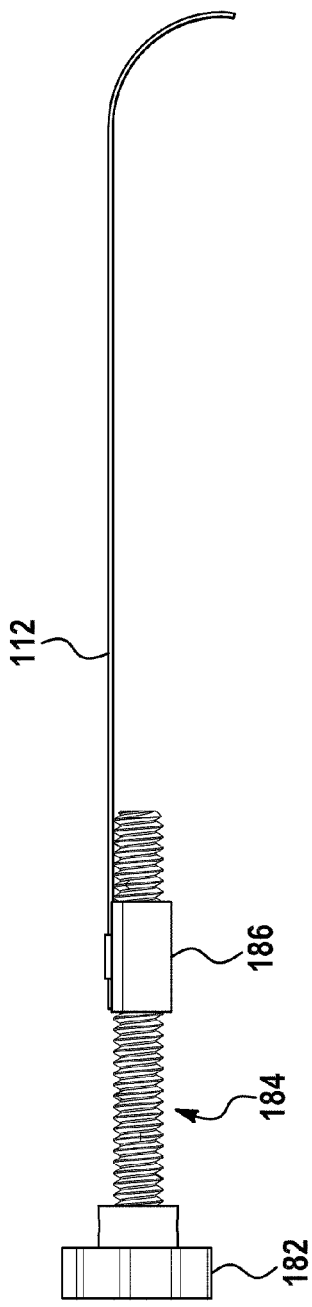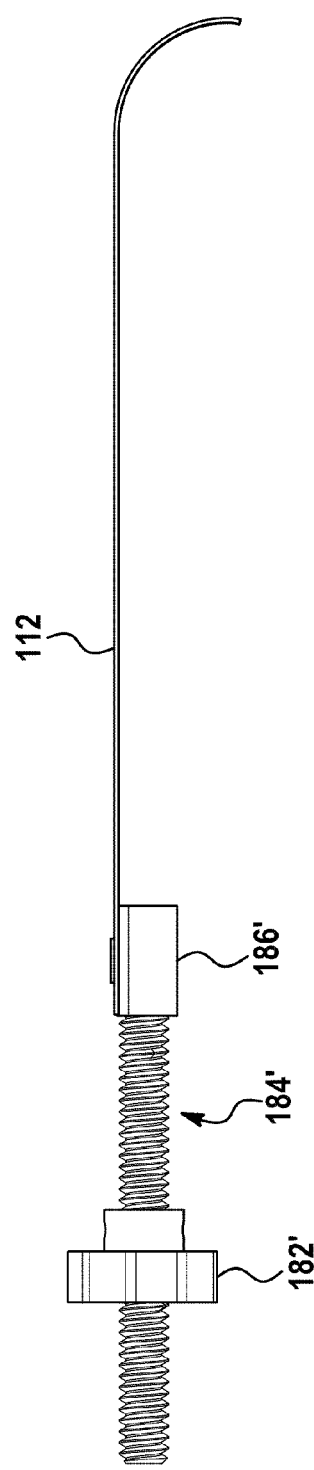

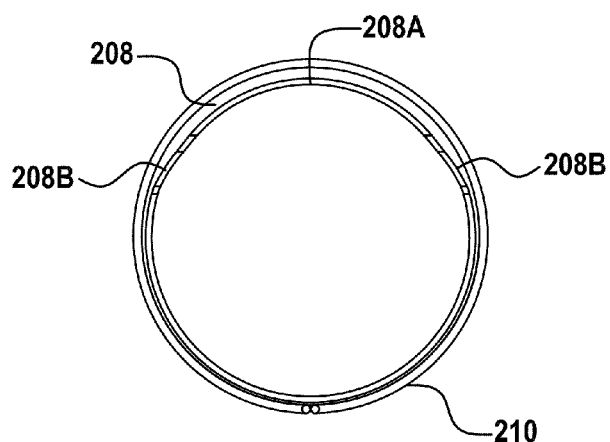
Figure 37A
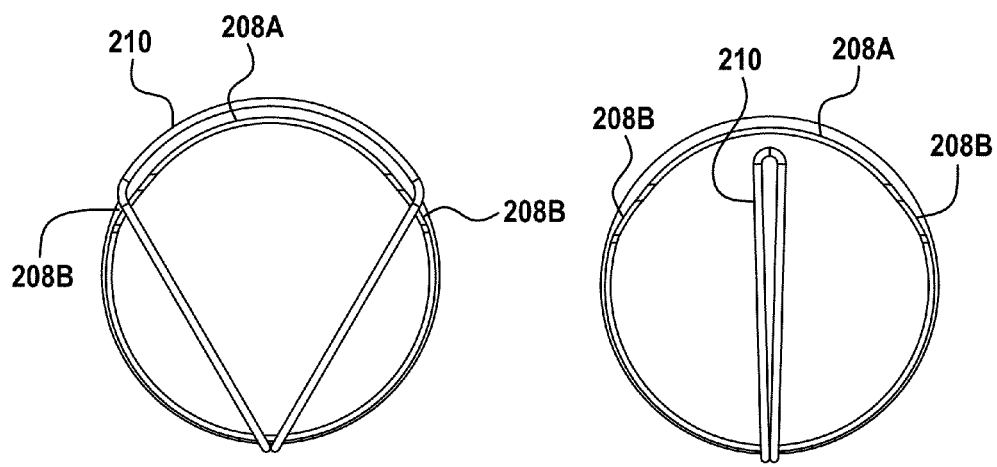
Figure 37B
Figure 37C

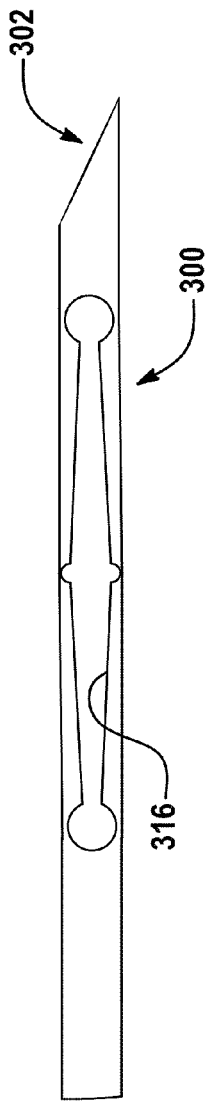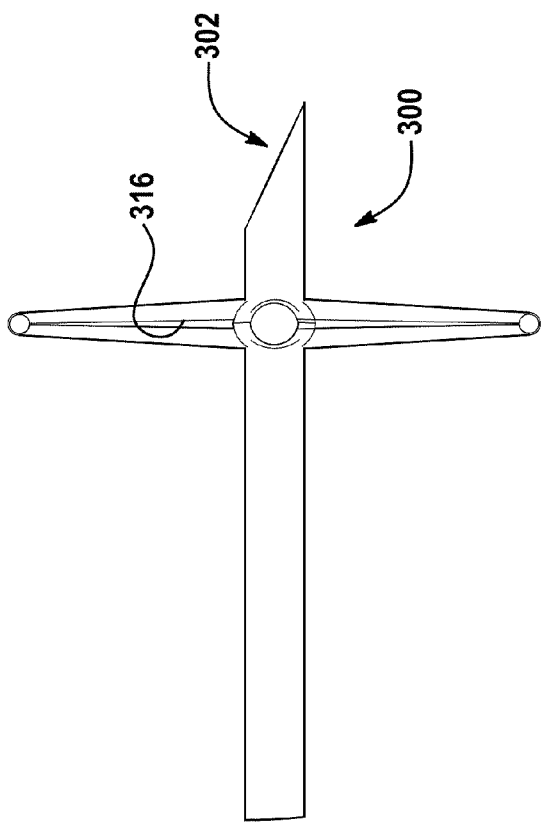
Figure 47 A
Figure 47 B

TISSUE EXCISION DEVICE WITH A COLLAPSIBLE STYLET

RELATED APPLICATIONS

The present application claims priority to U.S. Provisional Patent Application Ser. Nos. 61/319,159; 61/319,160; 61/319,162; 61/319,155; 61/319,148; 61/319,157; 61/319,209; 61/319,210; 61/319,217; 61/319,218; 61/319,223; 61/319,528 and 61/324,172, filed Mar. 30, 2010; Mar. 30, 2010; Mar. 30, 2010; Mar. 30, 2010; Mar. 30, 2010; Mar. 30, 2010; Mar. 30, 2010; Mar. 30, 2010; Mar. 30, 2010; Mar. 30, 2010; Mar. 30, 2010; Mar. 31, 2010 and Apr. 14, 2010, respectively, all of which are hereby incorporated by reference.

FIELD OF THE INVENTION

The present invention relates generally to surgical instruments, and more particularly, to a device for percutaneous excision of tissue, percutaneous excisional breast biopsy or percutaneous incisional breast biopsy.

BACKGROUND OF THE INVENTION

Generally, to date there have been two coring type, excisional breast biopsy devices developed and marketed. These devices are described in the following U.S. Pat. Nos. 5,111,828; 5,197,484; 5,353,804; 6,080,113; 6,267,732; 6,383,145; 6,551,253; 5,782,775; 5,817,034; 5,857,982; 6,036,657; 6,077,231; 6,165,137; and 6,213,957, all of which are hereby incorporated by reference.

These devices were originally developed for use with stereotactic imaging equipment. Generally, these devices use the same basic technology. The device disclosed in the '253 patent is exemplary. The biopsy device includes a localization needle with a guide wire preloaded into the device. The localization needle and guide wire are used to locate and localize the target area. The methodology of their usage can be summarized as follows:
1. Localize the target area with needle/wire hook;
2. Translate device up to the target area using a bladed stylet;
3. Core out the target specimen using a bladed cannula; and
4. Transect the tissue using a garrote wire to release the specimen.

The device can either by a handheld device or may be a fixed device. The below more detailed description of the method of using a prior art device is described with respect to a handheld device.

First, a localization needle is placed at the center of the target tissue. A localization wire is used to fix the handheld device to the tissue. After the localization wire is deployed, a stylet is manually advanced to a point just proximal of the target.

One problem associated with the current device is that the localization hook has very little holding power.

Another issue related to the prior art devices is the potential of the stylet to push and/or compress, i.e., the tissue in front of the stylet, i.e., "snowplow".

After the stylet reaches the target tissue, the cannula is manually advanced over the target tissue. With the cannula advanced over the target tissue, a mechanism, such as a garrote wire is activated to sever the target tissue from the breast. With the target tissue severed from the breast, the device, along with the target tissue with the cannula, may be removed.

Generally, these prior art devices are purely mechanical devices, i.e., in other words, the coring cannula is advanced by hand. The surgeon or user rotates a knob that activates a gear system to rotate and advances the coring cannula. This results in a relatively slow, intermittent advance of the cannula due to the start/stop motion of the surgeon. The start/stop motion can increase patient discomfort, as well as produce an undesirable irregular specimen shape.

As discussed above, once the cannula has been advanced over the target tissue, a garrote wire may be used to cut the sample tissue (which is inside the cannula) from the breast so that it may be removed. The garrote wire has several limitations. Typically, the garrote wire traverse (at least partially) along the length of the device, then is bent at a 90 degree angle, after which it encircles an inner surface of the coring cannula. The right angle in the garrote wire results in requiring a large amount of force to pull on the garrote wire to transect the tissue sample. Additionally, the garrote wire is generally located a distance behind the cutting edge of the coring cannula. This results in a core of tissue which is cored by the coring cannula, which is not transected by the garrote wire, and thus remains in the breast. Furthermore, the garrote wire may tear the tissue rather than cutting the tissue. Additionally, dense tissue can be pushed aside rather than cut.

Another issue related to prior art designs is the size of the cutting edge of the cannula with respect to the stylet. Prior to entry of the device into the breast, a skin incision is made using a scalpel. This incision is generally just slightly wider than the diameter of the cannula. Once the incision is made, the stylet is advanced in the breast, up to the point where the coring blade is ready to enter the incision. At this point, the surgeon will use nerve hooks to grab the skin and open the incision to allow the cutting edge of the cannula to enter the breast. However, the process of using the nerve hooks to grab the skin to make the incision wider can be cumbersome and inefficient and can cause patient discomfort.

The current devices use a stylet with integral cutting blades. The flat stylet blades are fixed to the stylet which may result in several adverse conditions. First, the close proximity of the cutting edge of the stylet blades to the ramp or stylet tip results in the pushing or compression or other inadvertent movement of the tissue by the stylet. The prior designs also results in a fixed minimal proximal margin equal to the length of the stylet system.

The present invention is aimed at one or more of the problems identified above.

SUMMARY OF THE INVENTION

In a first aspect of the present invention, a biopsy device is provided. The biopsy device includes a housing, a coring cannula, and a stylet. The coring cannula has a distal end, a longitudinal axis and is centered on the axis. The coring cannula is coupled to the housing and rotatable about the axis. The distal end of the coring cannula having a cutting edge. The stylet has a tip containing at least one blade and a central passage. The tip has a recess located near a proximal end thereof and is movable between an initial configuration and a contracted configuration. The cutting edge of the coring cannula is within the recess when the tip is in the initial configuration. The tip is movable into the contracted configuration. The cutting edge of the coring cannula is exposed when the tip is in the contracted configuration.

In a second aspect of the present invention, a biopsy device is provided. The biopsy device includes a housing, a coring cannula, and a stylet. The coring cannula has a distal end, a longitudinal axis and is centered on the axis. The coring cannula is coupled to the housing and rotatable about the axis. The distal end of the coring cannula having a cutting edge. The stylet has a tip containing at least one blade and a central passage. The tip has a recess located near a proximal end thereof and is movable between an initial configuration and a contracted configuration. The cutting edge of the coring cannula is within the recess when the tip is in the initial configuration. The tip is movable into the contracted configuration. The cutting edge of the coring cannula is exposed when the tip is in the contracted configuration. The device further includes a localization needle, a motor assembly, a variable speed circuit coupled to the motor assembly, a forward/reverse switch, and a speed control trigger. The localization needle is slidably disposed within the central passage. The motor assembly is coupled to the coring cannula for controllably rotating the cannula. The forward/reverse switch is electrically coupled to the variable speed circuit for controlling the direction of movement of the cannula. The speed control trigger is electrically coupled to the variable speed circuit. The variable speed circuit responsively controls the speed and rotation of the cannula as a function of the forward/reverse switch and actuation of the speed control trigger.

BRIEF DESCRIPTION OF THE DRAWINGS

Other advantages of the present invention will be readily appreciated as the same becomes better understood by reference to the following detailed description when considered in connection with the accompanying drawings wherein:

FIG. 4A is a drawing of the independent needle assembly of FIG. 3;

FIG. 4B is another drawing of the independent needle assembly of FIG. 3;

FIG. 5A is a drawing of a guide element of the independent needle assembly of FIGS. 3 and 4;

FIG. 5B is a larger view of a portion of FIG. 5A;

FIG. 19A is an illustration of a partial view of an integrated needle assembly with a guide element in the unlocking configuration, according to an embodiment of the present invention;

FIG. 19B is an illustration of the integrated needle assembly of FIG. 19A with the guide element in the locking configuration;

FIG. 19C is an illustration of the integrated needle assembly of FIG. 19A with two three wires of the guide element retracted into the localization needle;

FIG. 19D is an illustration of a part of the guide element with a single wire which remains in the target tissue to provide orientation of the sample;

FIG. 20A is a partial side view of a coring cannula in an initial position and a final position, according to an embodiment of the present invention;

FIG. 20B is a front view of the coring cannula of FIG. 20A;

FIG. 21A is a partial side view of the coring cannula of FIG. 20B during initial advanced of a flexible transection blade;

FIG. 21B is a front view of the coring cannula and flexible transection blade of FIG. 21A;

FIG. 22A is a partial side view of the coring cannula and flexible transection blade in a second blade position;

FIG. 22B is a front view of the coring cannula flexible transection blade in the second blade position;

FIG. 30 is a graphical representation of a second alternative drivetrain in an initial position, according to an embodiment of the present invention;

FIG. 31 is a graphical representation of the second alternative drivetrain in a final position;

FIG. 37A is a first view of a garrote wire for use with the cutting ring of FIGS. 36A and 36B;

FIG. 37B is a second view of a garrote wire for use with the cutting ring of FIGS. 36A and 36B;

FIG. 37C is a third view of a garrote wire for use with the cutting ring of FIGS. 36A and 36B;

FIG. 47A is a first view of an expanding localization needle, according to an other embodiment of the present invention;

FIG. 47B is a partial view of the expanding localization needle of FIG. 47A;

DETAILED DESCRIPTION OF INVENTION

Referring to the Figures, wherein like numerals indicate like or corresponding parts throughout the several views, the present invention provides a breast biopsy device 10 and a method of operating the breast biopsy device 10.

Figure 1:
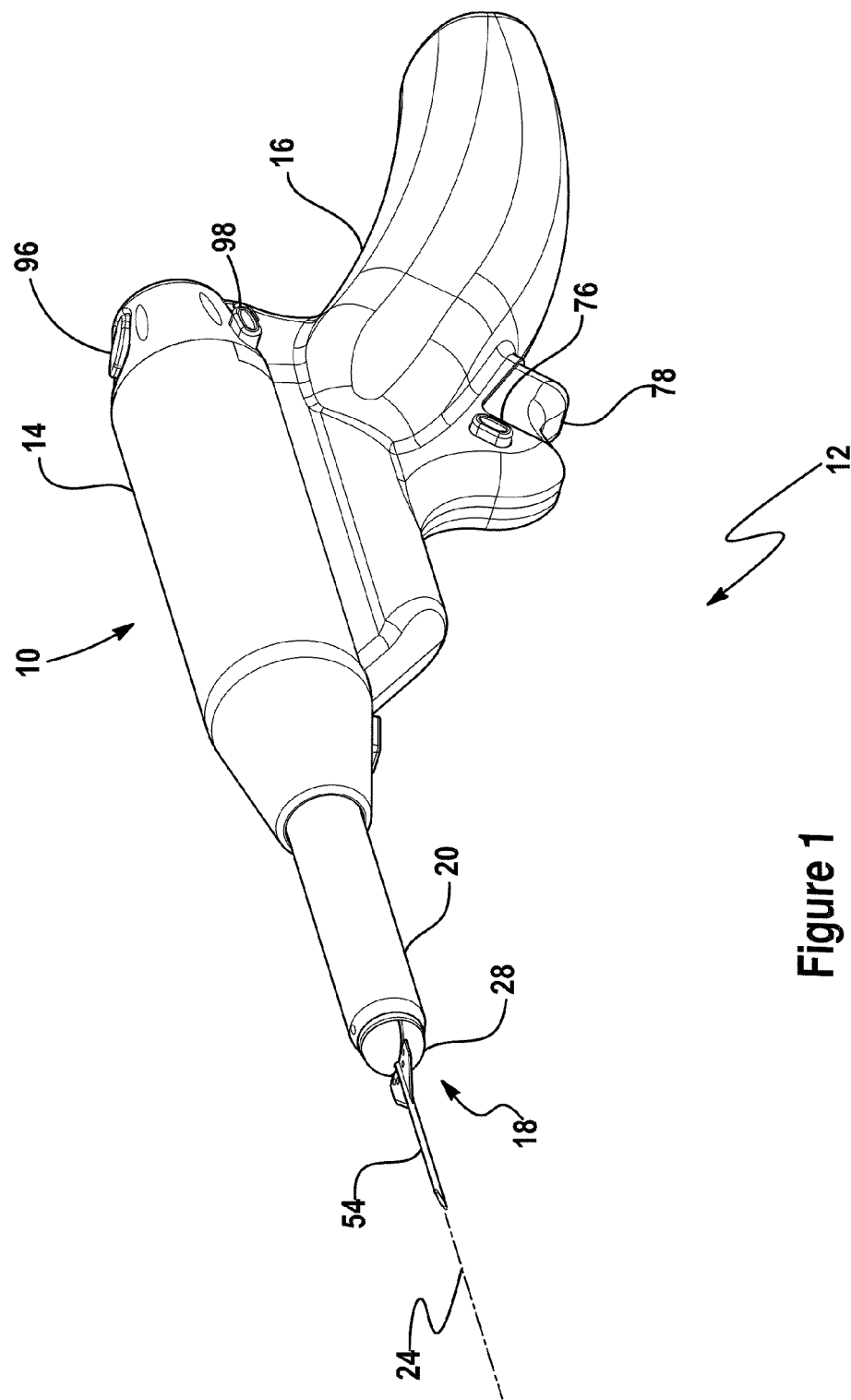
FIG. 1 is a drawing of a biopsy device with an integrated needle, according to an embodiment of the present invention.

With reference to FIG. 1, in one aspect of the present invention, the breast biopsy device 10 is embodied in a handheld device 12. It should be noted that the present invention may be embodied in a fixed device (not shown).

The handheld device 12 may include a housing 14 (see FIG. 10) and a handle 16. In one aspect, the housing 14 is removable from the handle 16. The handle 16 is reusable. The housing 14 (and all parts contained therein) are disposable and generally provided sterile. In one aspect of the present invention, the device 10 may include an integrated needle assembly 18 (described below). In another aspect of the present invention, the device 10 may include an independent needle assembly 18' (described below).

Figure 10:
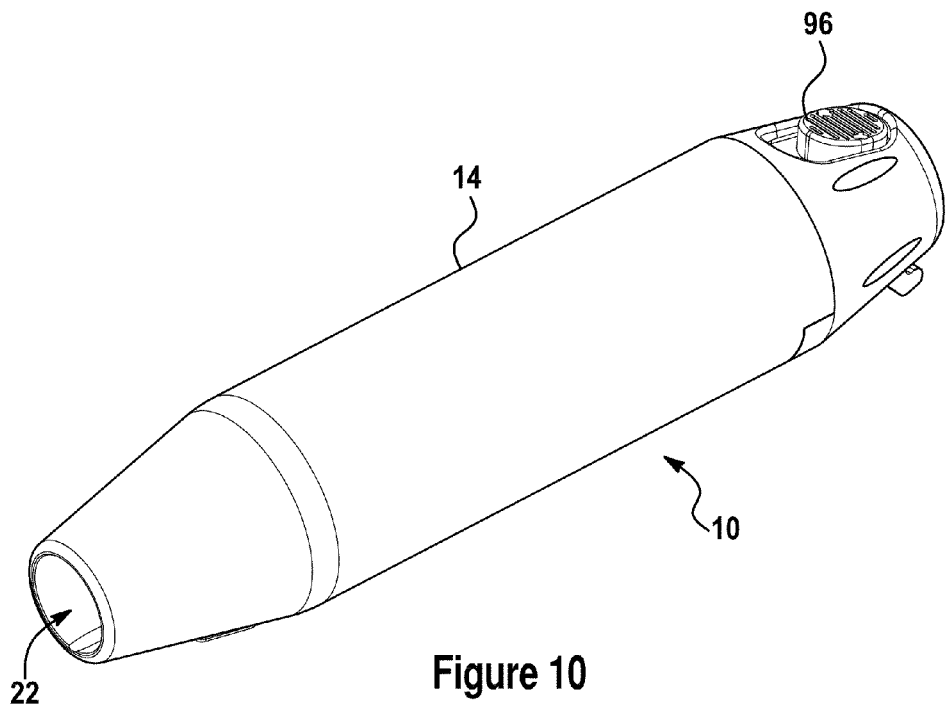
FIG. 10 is a drawing of the housing, according to an embodiment of the present invention.
Figure 11:
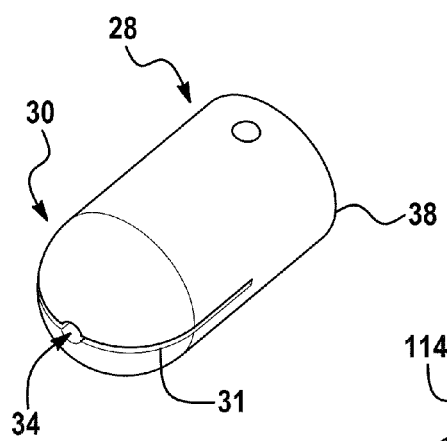
FIG. 11 is a drawing of the stylet, according to an embodiment of the present invention.
Figure 12:
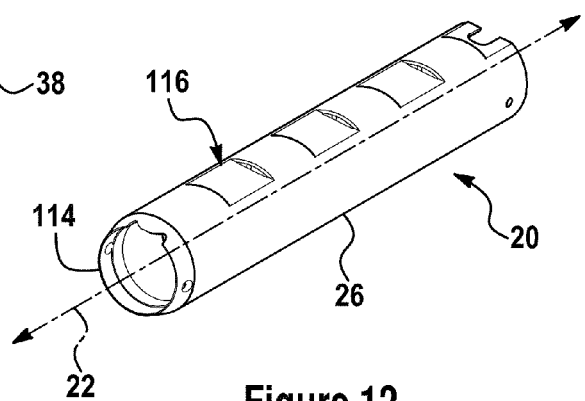
FIG. 12 a drawing of the cannula, according to an embodiment of the present invention.

With particular reference to FIGS. 10, 11 and 12, the housing 14 may include an inner passage 22 (see FIG. 10). A coring cannula 20 is slidably mounted within the inner passage 22 of the housing 14. The coring cannula 20 has a longitudinal axis 24 and may include a shaft 26 centered on the axis 24.

In one embodiment, the coring cannula 20 is coupled to the housing such that rotational movement of the coring cannula 20 about the axis 24 results in linear movement of the coring cannula 20 along the axis 24. As discussed more fully below, the coring cannula 20 has a cutting edge allowing it to cut through tissue as it is rotated and advanced.

It should be noted that in other embodiments, the coring cannula 20 may simply rotate within the housing 14. Linear movement of the coring cannula 20 (to advance the device 10 and the coring cannula 20 into the breast) may be provided by external mechanical means or by the user.

The breast biopsy device 10 includes a stylet 28, which includes a stylet housing 38. With particular reference to FIG. 11, the stylet includes a tip 30. The tip 30 includes at least one blade 32 and a central passage 34. The tip 30 may also include a slot 31 for the at least one blade 32.

In one embodiment of the present invention, the stylet 28 is mounted within the coring cannula 20. The stylet 28 includes first and second blades 32A, 32B integrated between two half portions 38A, 38B of a stylet housing 38. The stylet 28 transects, dilates, and separates tissue as the device 10 is inserted or advanced towards the biopsy site.

A drive assembly 40 mounted within the housing 14 and the handle 16 (see FIGS. 7 and 9) rotates the cannula 20 and controllably rotates the cannula 20. In one embodiment, the drive assembly 40 also moves the cannula 20 in a direction parallel to (and along) the axis 24. In one aspect, the coring cannula 20 has a predetermined linear advancement per revolution of the coring cannula 20. In one embodiment, the predetermined linear advancement is 0.50 inches per revolution. In an other embodiment, the predetermined linear advancement is 0.84 inches per revolution.

Figure 9:
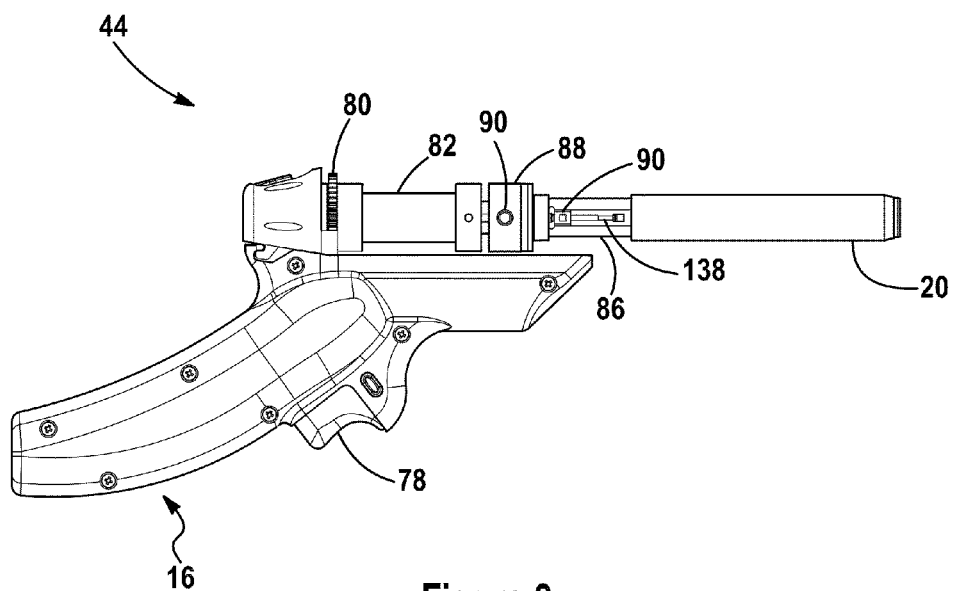
FIG. 9 is a second cut-away view of the breast biopsy device of FIG. 8.

The drive assembly 40 may include a motor assembly comprised of a DC motor and step down transmission 42 and a drivetrain 44. The DC motor and step down transmission 42 is coupled to the drivetrain 44 (FIG. 9). The drive assembly 40 and the drivetrain 44 are explained more fully below.

In one aspect of the present invention, the drive assembly 40 rotates the coring cannula 20 as a single speed, for example, at or around 80 revolutions per minute. Alternatively, the drive assembly 40 rotates the coring cannula 20 at a variable speed (see below).

The needle assembly 18, 18' may include a localization needle 54. The localization needle 54 has an inner channel 56 and is slidably removable from the central passage of the stylet 28. The needle assembly 18, 18' further includes a guide element 52 (see FIGS. 4 and 5A). The guide element 52 is used to secure the tissue while the coring cannula 20 is advanced.

In one embodiment of the present invention, the guide element 52 has a first end 58 and a second end 60. The first end 58 of the guide element 52 is slidably disposed within the channel 56 of the localization needle 54.

In one embodiment, the guide element 52 is composed, at least in part, of a metal alloy. In one embodiment, the metal alloy is composed of nickel and titanium. In one embodiment, the metal alloy is nitinol.

A locking member 62 is formed at the second end 60 of the guide element 52. The locking member 62 has an unlocking configuration and a locking configuration. The locking member 62 is in the unlocking configuration when the guide element 52 is in the first position, i.e., fully contained within the localization needle 54 (see FIG. 13B). The locking member 62 is in the locking configuration when the guide element 52 is in the second position, i.e., then the locking member 62 is outside of the localization needle 54 (see FIG. 13C). In the illustrated embodiment, the locking wire 62 is formed of multiple wires 64, e.g., two, which are predisposed toward the locking configuration. When the guide element 52 is slid back into the localization needle 54, the inner channel 56 of the localization needle 54 constrains and confines the wires 64 in the unlocking configuration. Once the guide element 52 is slid towards and into the second position, the wires 64 are freed from the constraints on the localization needle 54 and allowed to move toward and into the locking configuration.

In one aspect of the present invention, the locking configuration is defined by a predefined shape of the wires 64. In one embodiment, the predefined shape is a hook shape.

In one embodiment, wires (not shown) may be wrapped around the wires 64 to provide rigidity to allow the guide element 52 to be moved within the localization needle 54. The number of wires 64, as well as the diameter of the wires 64 (and wires used to provide rigidity) is optimized to provide maximize holding and as a function of the type of targeted tissue, e.g., hard or soft tissue.

Figure 14:
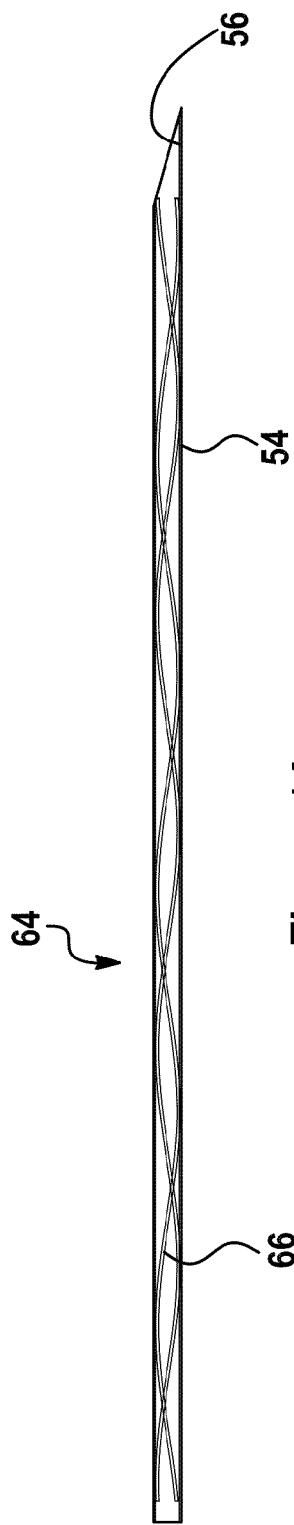
FIG. 14 is an illustration of a guide element according to a second embodiment of the present invention, in the unlocking configuration.
Figure 15:
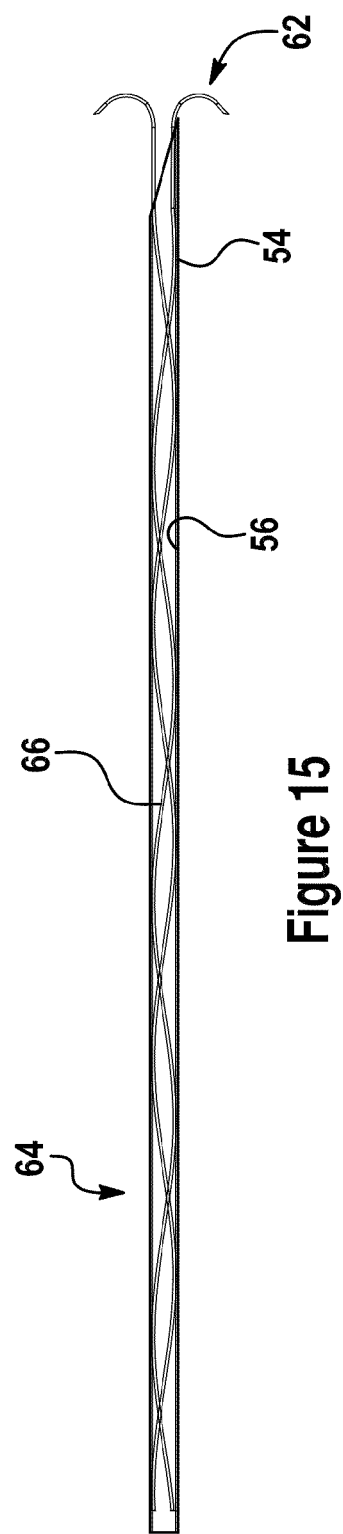
FIG. 15 is an illustration of the guide element of FIG. 14A in the locking configuration.
Figure 16:
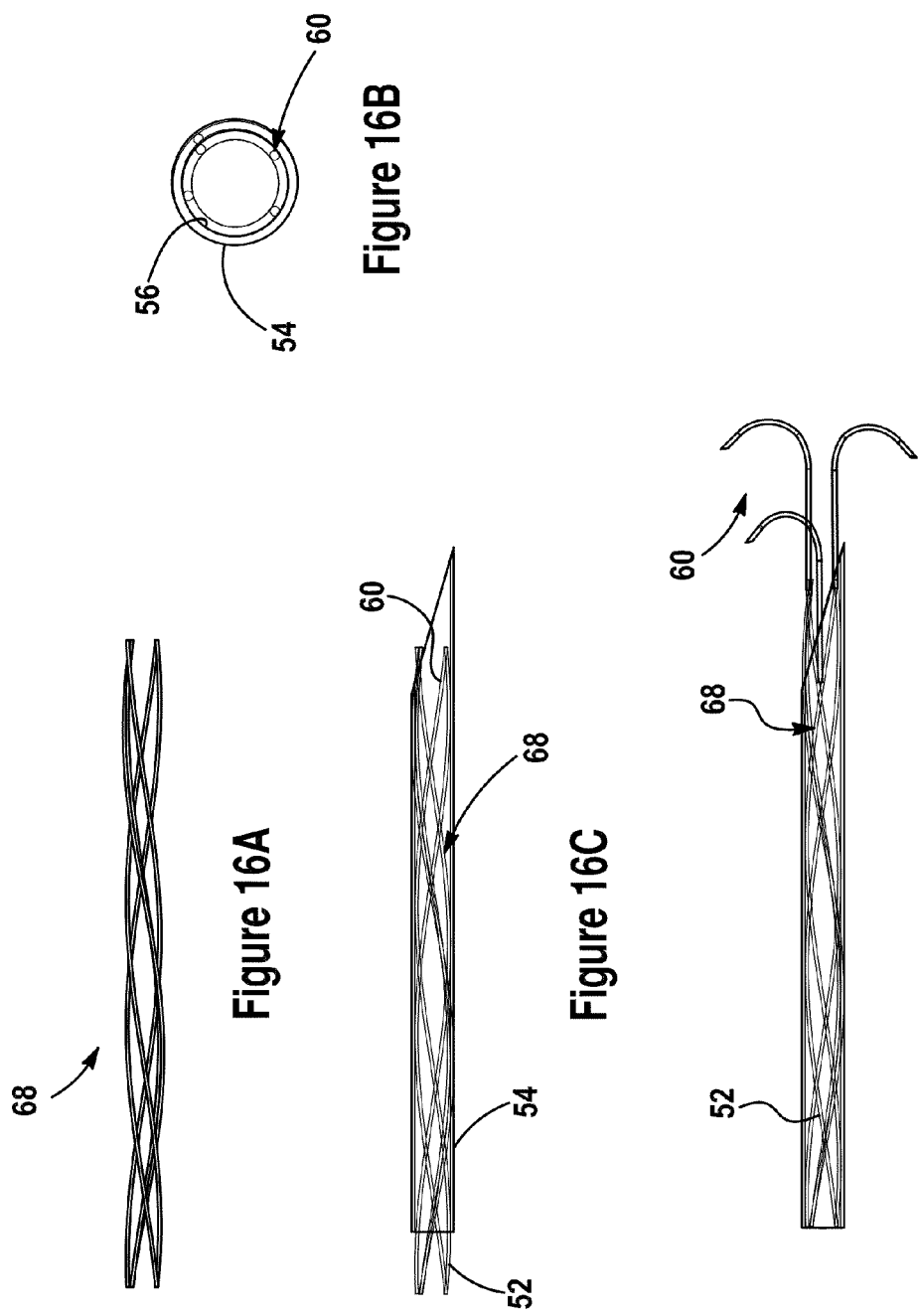
FIG. 16A is an illustration of a guide element according to a fourth embodiment of the present invention.
FIG. 16B is a front view of the guide element of FIG. 16A in the unlocking configuration.
FIG. 16C is a side view of the guide element of FIG. 16A in the unlocking configuration.
FIG. 16D is a side view of the guide element of FIG. 16A in the locking configuration.

With reference to FIGS. 14 and 15, in another embodiment of the present invention, the locking member 62 may include a twisted pair of wires 66. The guide element 52 is shown in the first position in FIG. 14 with the twisted pair of wires 66 in the unlocking configuration. The guide element 52 is shown in the second position in FIG. 15 with the twisted pair of wires 66 in the locking configuration.

With reference to FIGS. 16A, 16B, 16C, and 16D, in another embodiment of the present invention, the locking member 62 is formed from braided wire or cable 68. As shown, in one embodiment, the distal ends of the cables may be straightened and then formed into a predetermined shape, such as a hook shape. The number of wires or cables may vary, e.g., the braided wire or cable may include 4, 7 or any number of individual wires or cables. The guide element 52 is shown in the first position in FIG. 16C with the braided cable 68 in the unlocking configuration. The guide element 52 is shown in the second position in FIG. 16D with the braided cable 68 in the locking configuration.

Figure 17:
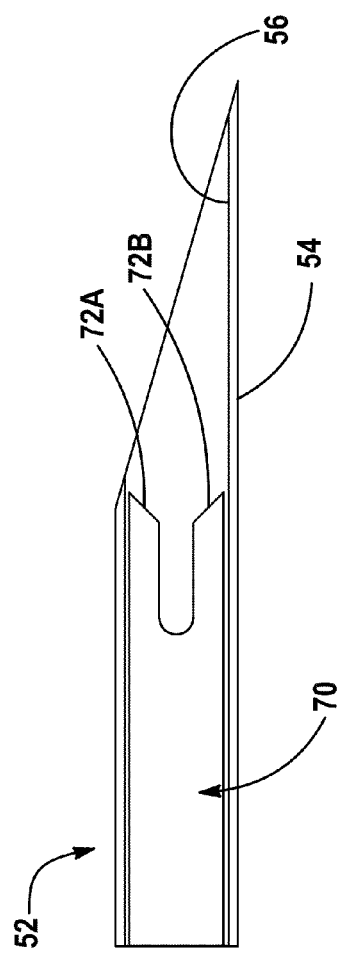
FIG. 17 is a side view of a guide element according to a fifth embodiment of the present invention.
Figure 18:
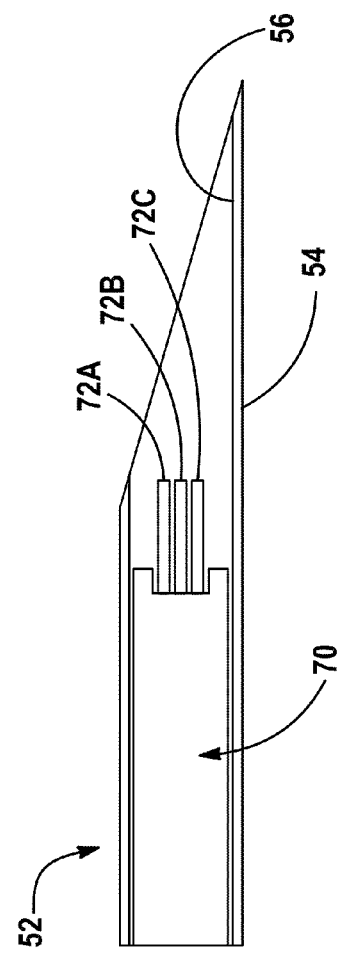
FIG. 18 is a side view of a guide element according to a sixth embodiment of the present invention.

With reference to FIGS. 17 and 18, in another embodiment, the guide element 52 may include a pushrod 70 and at least two flexible fingers 72A, 72B. In one embodiment, the pushrod 70 and flexible fingers 72A, 72B are unitarily formed (FIG. 17). In another embodiment, the flexible fingers 72A, 72B are affixed to the pushrod 70 (FIG. 18).

In one aspect, the flexible fingers 72A, 72B may be predisposed towards the locking configuration through a heat treat process.

Returning to FIGS. 7 and 9, in one embodiment of the present invention, the drive assembly 40 may include a variable speed circuit 74 electrically coupled to the motor assembly 42, 44. A forward/reverse switch 76 is electrically coupled to the variable speed circuit 74. A speed control trigger 78 is electrically coupled to the variable speed circuit 74. The forward/reverse switch 76 controls the direction of the DC motor 42, and thus, the direction of movement (forward/reverse) of the cannula 20 along the axis 24.

The variable speed circuit 74 controls the speed and rotation of the cannula 20 as a function of the forward/reverse switch 76 and actuation of the speed control trigger 78. In one aspect, the variable speed circuit 74 has a predetermined speed range, for example 0-100 revolutions per minute.

The DC motor and transmission 42 is powered by a rechargeable battery 46, which may be charged via an external power source (not shown) through recharging port 48. In one embodiment, the rechargeable battery 46 is a lithium ion battery.

The DC motor and transmission 42 is used to provide low speed and high torque to the drivetrain 44. A drive gear 50 is directly coupled between the motor 42 and the drivetrain 44.

Figure 7:
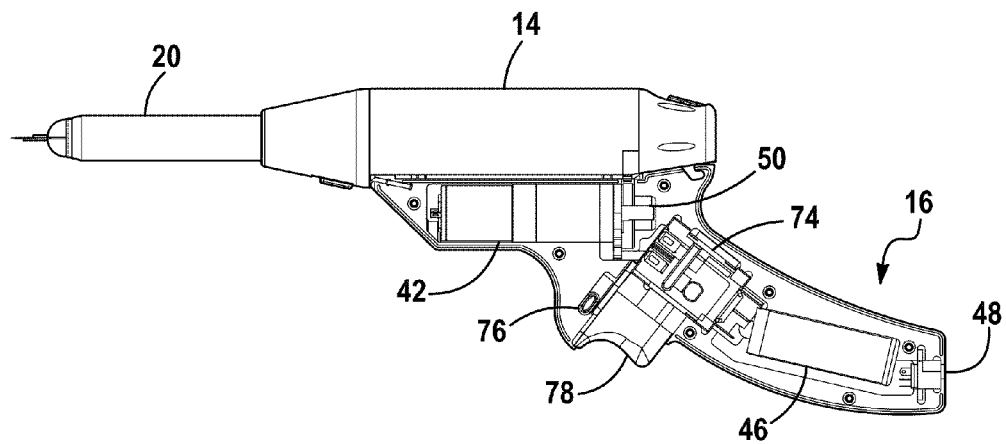
FIG. 7 is a cut-away view of the handle of a breast biopsy device, according to an embodiment of the present invention.
Figure 8:
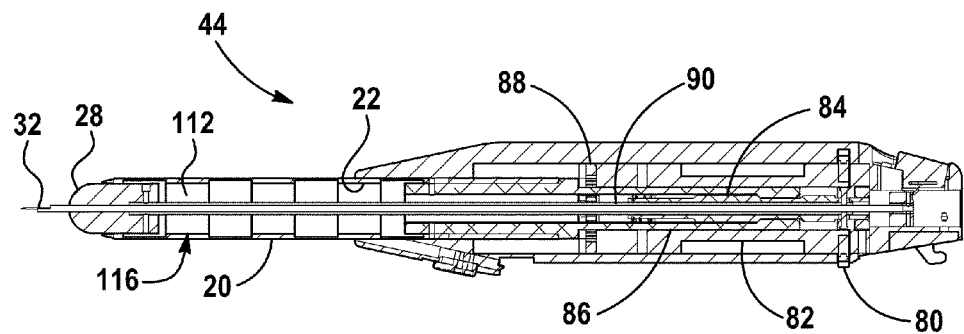
FIG. 8 is a first cut-away view of a breast biopsy device illustrating the drivetrain components, according to an embodiment of the present invention.

With specific reference to FIGS. 7, 8, and 9, the drivetrain 44 may include a spline gear 80, a spline gear support 82, a lead screw 84, a shaft 86, and a ring gear transmission 88. The spline gear 80 is contained with the housing 14 and is supported by the spline gear support 82. The drive gear 50 engages the spline gear 82 to transfer power to the drivetrain 44, and thus, the coring cannula 20.

The speed of the DC motor 42 is controlled by user actuation of the speed control trigger 78. The variable speed circuit 74 enables variable speed ramp up and slow down. In one embodiment, a speed range of approximately 0-100 rpm at the cannula may be provided.

The drivetrain 44 is contained within the housing 14, which is removable coupled to the handle 16. When the device 10 is assembled, the spline gear 80 engages the drive gear 50 within the handle 16. Power transferred through the drive gear 50 causes rotation of the spline gear 80. The spline gear 80 is attached to the spline gear support 82. The spline gear support 82 is keyed to the shaft 86. The spline gear support key 82 provides rotation to the shaft 86 while allowing it to move axially (along axis 24). The lead screw 84, which is fixed to the housing 14, is engaged with threads at the proximal end of the shaft 86. The coring cannula 20 is attached to the shaft 86. As the shaft 86 is rotated, the threaded engagement with the lead screw 84 creates axial movement of the coring cannula 20.

As the cannula 20 rotates, it continues to move forward for a distance determined by the thread length on the lead screw 84. As the shaft 86 reaches the end of the threads, it will continue to rotate, but will no longer move forward. The timing is designed such that when the shaft 86 reaches the end of the threaded section of the lead screw 84, the transmission lockout (lock out button 90) engages. With the lock out button 90 engaged, the ring gear assembly 88 is activated and begins to advance a drive dog 92 forward along the drive screw 50.

The drive dog 92 is coupled to a severing mechanism 94 which is used to sever the tissue contained within the coring cannula 20, which is described more fully below.

The general process of utilization of the device will now be described. First, the localization needle 54 is advanced into the breast under ultrasound guidance. In one aspect of the present invention, this is performed manually. For instance, with the handheld device 10, the user manually inserts the needle 54 by positioning and manually moving the device 10. When the needle 54 reaches the target area, the tissue anchor or locking member 62 is advanced to secure the tissue prior to advancement of the device 10. Next, the localization needle 54 is released allowing the device 10 to move independently of the needle 54. The device 10 is now advanced into the breast, with the stylet blades 32 separating the tissue up to the target area. When the device 10 has reached the target area, the coring cannula 20 is advanced. The cannula 20 is advanced by depressing the speed control trigger 78 on the handle 16, with the forward/reverse switch 76 in a forward position. When the cannula 20 reaches its full core length, the severing mechanism 94 is actuated, separating the tissue core from surrounding tissue. In one embodiment, the severing mechanism 94 may include a flexible blade (see below) will automatically advance from the distal end of the coring cannula 20. After the core of tissue has been cut free, the device 10 is removed from the breast. With the device out of the breast, the forward/reverse switch 76 is placed in a reverse position and the flexible blade is retracted using the speed control trigger 78 allowing the tissue sample to be retrieved from the coring cannula.

Figure 2A:
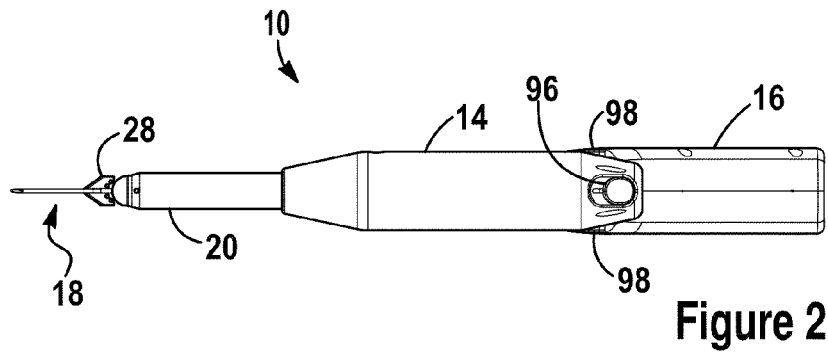
FIG. 2 includes a series of views of the biopsy device of FIG. 1 illustrating operation thereof.
Figure 2B:
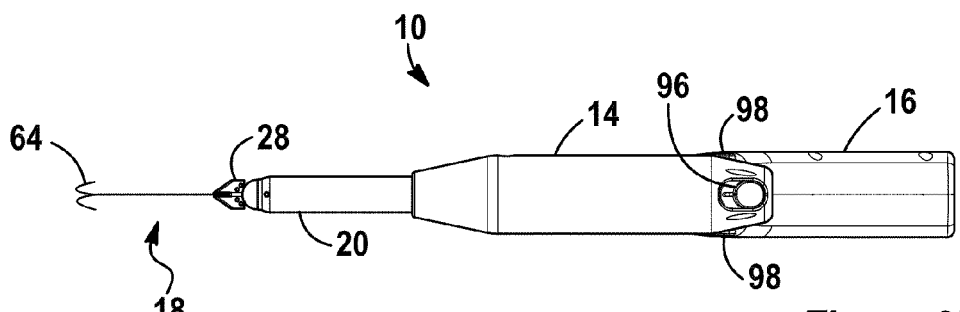
Figure 2C:
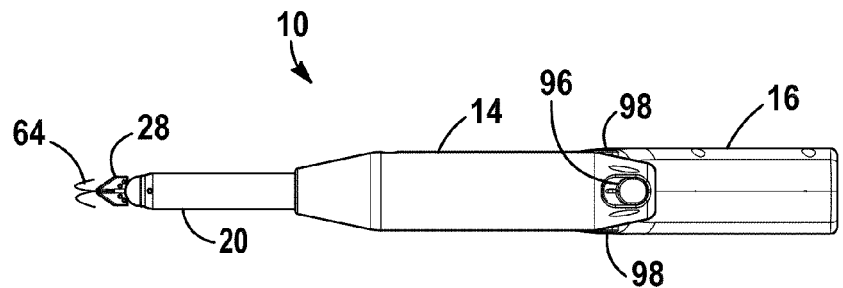
Figure 2D:
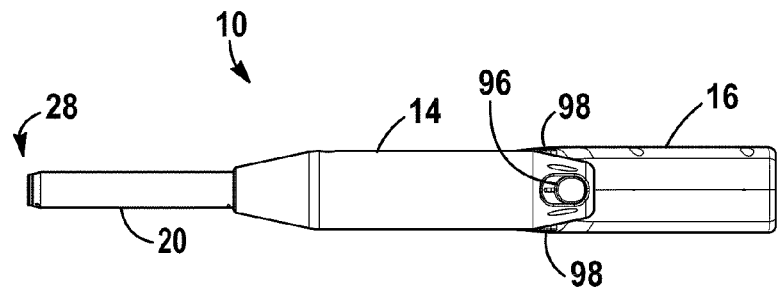
Figure 3:
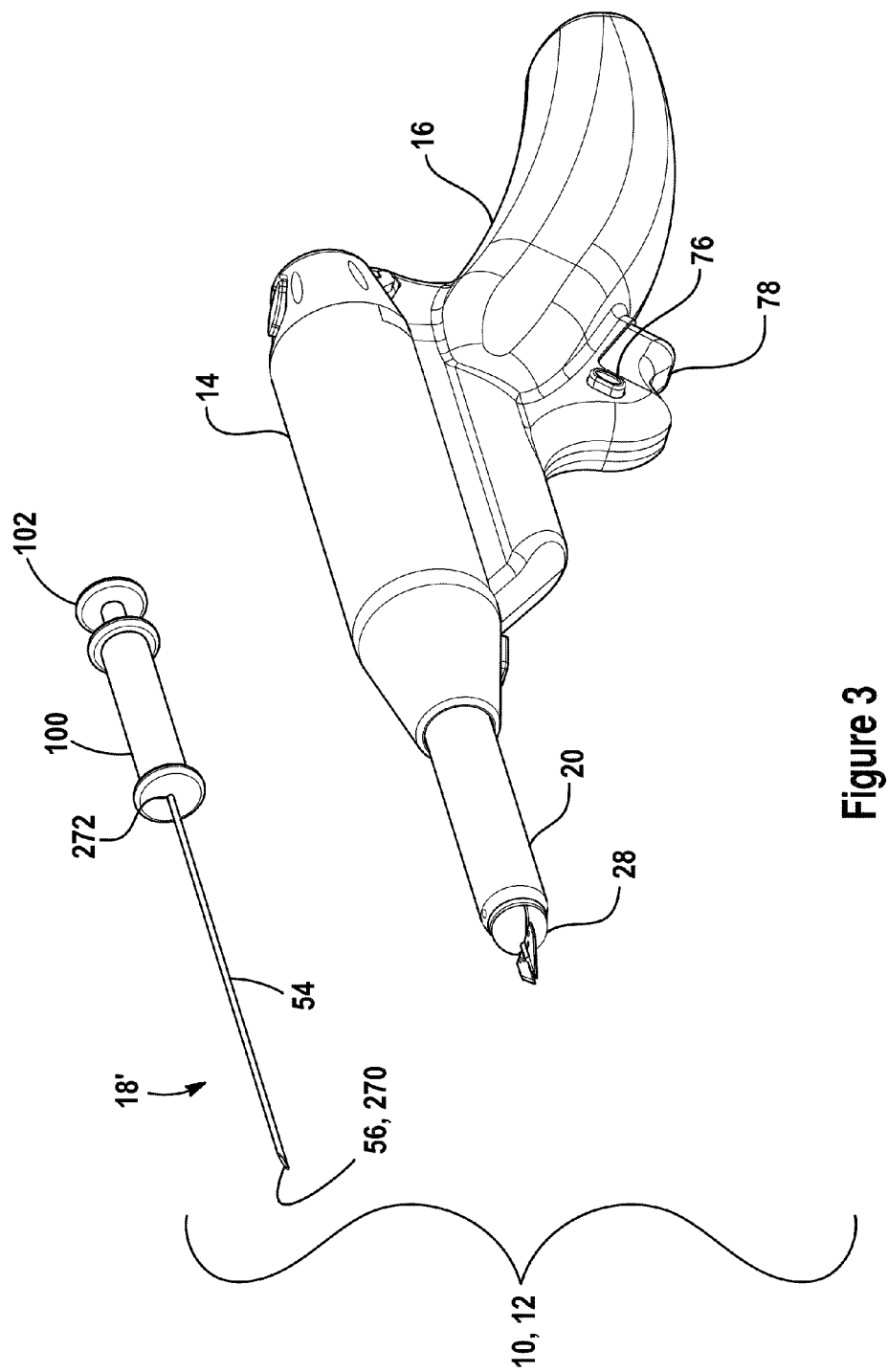
FIG. 3 is an isometric drawing of a biopsy device with an independent needle assembly, according to an alternative embodiment of the present invention.
Figure 6:
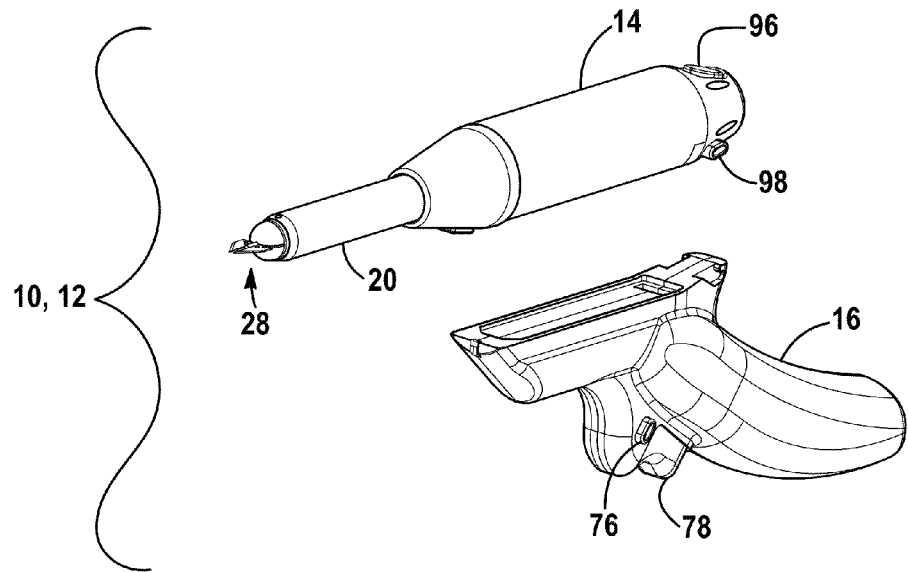
FIG. 6 is a isometric illustration of a handheld breast biopsy device having a housing and a handle, according to an embodiment of the present invention.

As stated above, in one aspect of the present invention, an integrated needle assembly 18, as shown in FIG. 1 and demonstrated in FIGS. 2A, 2B, 2C, and 2D, may be provided. With the integrated needle assembly 18, the needle assembly 18 and the coring cannula are integrated into a single unit 18, 20 (see FIG. 2A). With the integrated needle assembly 18, the needle assembly 18 is inserted within the central passage 34 of the stylet housing 38 when the localization needle 54 is inserted into the breast (FIG. 2B). Once the localization needle 54 reaches the target tissue, a locking member actuation button 96, located on the top of the housing 14 is slid forward. The actuation button 96 is linked to the locking member 62 resulting in the locking member 62 being slid out of the localization needle 54 securing the target tissue.

Once the target tissue is secured, the localization needle 54 and locking member 82 are released from the housing 14 by actuation of one of the localization needle release button(s) 98 located thereon. This allows the device 10 to be slid up localization needle 54 (the stylet blades 32 separating the tissue allowing the stylet 28 and coring cannula 20 to pass. Once the coring cannula 20 is adjacent the target tissue, the process proceeds as above.

Then, the device 10 would be fed down the guide rod 104 and the process would proceed as above (see FIG. 5A).

With respect FIG. 5B, the central passage 34 is formed by the stylet tube 36. The stylet tube 36 includes an opening 106 which allows the needle assembly 18, 18B' to pass into the central passage 34. The stylet tube 36 also may include a guide portion 108 which extends past the opening 106 to assist in the placement of the guide rod into the central passage 34.

In another aspect of the present invention, an independent needle assembly 18' may be provided (see FIGS. 3, 4A, 4B, 5A, 5B). The independent needle assembly 18' is separate from the coring cannula 20. The independent needle assembly 18' includes a localization needle 54', an independent needle handle 100, and a plunger 102. The localization needle 54' is inserted into the breast tissue using the handle 100. Once the target tissue is reached, the plunger 102 is pushed forward. The locking member 62 is pushed forward by the plunger 102, pushing the wires 64 into the target tissue, thereby securing the target tissue. The localization needle 54' (and handle 100), may thereafter be removed, leaving the locking member 62 within the breast with a guide rod 104 extending out of the breast (see FIG. 4B).

The localization needle 54' has a first end 54A' and a second end 54'. The localization needle includes an internal channel or bore 56. The handle 100 has first and second ends 100A, 100B and an internal bore 268. The first end 54A of the needle 54' is fixed to the second end of the handle 100B. The internal bore 56 of the needle 54' and the internal bore 268 of the handle 100 form an assembly bore 270 therethrough. In the illustrated embodiment, the guide element 52 has a guide rod 104 and a locking member 62. The guide element 104 has first and second ends 58, 60 and is removably contained within the assembly bore 270. The locking member 62 is fixed to the second end 60 of the guide rod 104. The plunger 102 includes a pushrod 102B and an actuation element 102A coupled to the pushrod 102B. The plunger 102A is movable from a first state (FIG. 4A) to a second state (FIG. 4B) One end of the pushrod 102B acts on the first end 58 of the guide rod 104, forcing the locking member 62 out of the needle 18' as the pushrod 102 is moved from the first state to the second state.

With reference to FIGS. 19A-19D, in one embodiment one of the wires 64' from the locking member 62 is detachable from the pushrod 70. It should be noted that although FIGS. 19A-19D illustrated this feature with respect to the independent needle assembly 18, the detachable wire 64' concept may also be used with the integrated needle assembly 18'.

As shown in FIG. 19A, the locking member 62 is contained within the localization needle 54 when the localization needle is initially inserted into the breast tissue. When the localization needle 54 reaches the target tissue, the locking member 62 is deployed as discussed above (FIG. 19B) to secure the target tissue. Then the cannula 20 is advanced over the target tissue and severed using the severing mechanism 94 (see above). Once the device 10 has been removed from the breast, the localization needle 18' may be used to push the severed tissue from the cannula 20. The tissue anchors or wires 64 may then be retracted. The third hook 64' may either not be attached to the pushrod 70 or may be detachable therefore. The third hook or wire 64' remains attached or secured to the tissue to provide an orientation marker for the sample during pathology (see FIG. 19D).

Figure 13A:
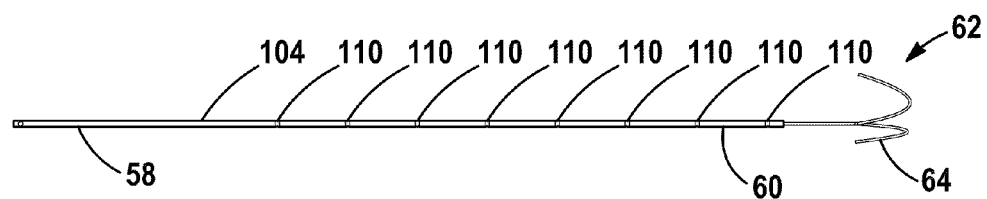
FIG. 13A is an illustration of a guide element of an independent needle assembly, according to a first embodiment of the present invention.
Figure 13B:
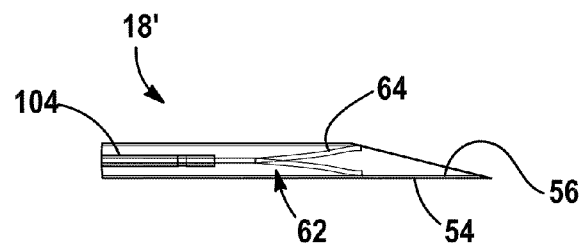
FIG. 13B is an illustration of a partial view of the independent needle assembly of FIG. 13A, in the unlocking configuration.
Figure 13C:
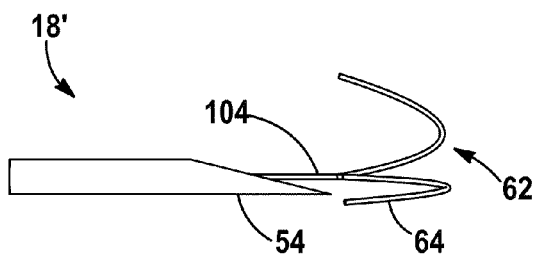
FIG. 13C is an illustration of a partial view of the independent needle assembly of FIG. 13A, in the locking configuration.

In another aspect of the present invention, the guide rod 104 may include scale markings 110 to provide an indication to the user the depth of the anchor/guide element 52 within the breast, as shown in FIGS. 13A and 19B.

In another aspect of the present invention, the biopsy device 12 includes a flexible transection blade 112. The flexible transection blade 112 is a flat metal blade with one end sharpened is formatted to the required radius (see below). The blade thickness and material properties as such that the formed flexible transection blade 112 can be flattened out will "spring" back to its formed shape. The blade 112 will be held in a flat position along the side of the coring cannula.

The coring cannula 20 will use an angled or non-continuous cutting ring (see below) at the completion of the coring process. As shown in FIGS. 20A and 20B, the coring cannula 20 is movable along the axis 24 from an initial cannula location 118 (shown in dotted lines) to a final cannula location 120 in response to rotation of the coring cannula 20 about the axis 24 in a first direction.

In one embodiment, once the coring cannula 20 reaches the final cannula location 120, it will continue to rotate but will not advance axially forward. A mechanism 122 will be engaged to drive the flexible transection blade 112 forward. The flexible transection blade 112 exits the coring cannula 20 at a point slightly distal to the cutting edge of the coring cannula 20 (see FIGS. 21A and 21B). As the flexible blade 112 is driven out of the cannula 20, it will begin to return to its pre-formed curvature. Since this advancement is taking place while the coring cannula 20 is rotating, the result will be a curved, complete cut through the tissue. The path of the blade 112 is designed to intersect with the distal end of the cutting path from the coring cannula 20, resulting in complete transection and release of the tissue specimen.

Figure 23A:
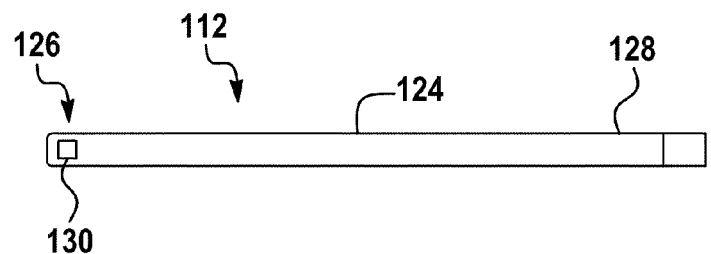
FIG. 23A is a view of the flexible transection blade in an initial configuration, according to an embodiment of the present invention.
Figure 23B:
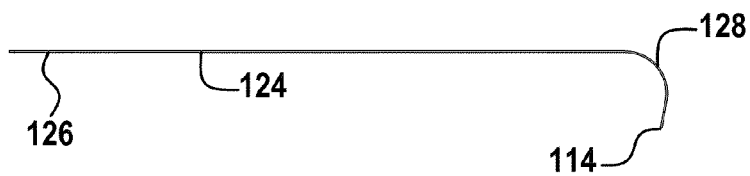
FIG. 23B is a top view of the flexible transection blade in a cutting configuration, according to an embodiment of the present invention.
Figure 23C:
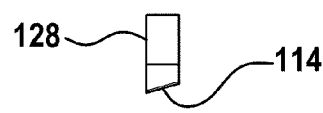
FIG. 23C is a front view of the flexible transection blade in the cutting configuration showing a cutting edge, according to an embodiment of the present invention.

With reference to FIGS. 23A, 23B, and 23C, in one embodiment the flexible transection blade 112 consists of a thin strip 124 of spring steel or nitinol. The flexible transection blade 112 has a first end 126 and a second or distal end 128. The flexible transection blade 112 is coupled to the coring cannula 20 at the first end 126. The distal end 128 of the flexible transection blade 112 is cut to an optimized angle and sharpened to a cutting edge 114 (see FIG. 23C). A hole mount 130 may be provided for mounting the blade 112 to the drive assembly 40.

In one embodiment as shown in FIGS. 8 and 9, the flexible transection blade 112 is stored in a channel 116 built into the coring cannula 20. The flexible transection blade 112 is held flat in this stored position. At the completion of the coring process, the coring cannula 20 will cease axial advancement, but will continue to rotate. During this rotation the flexible blade 112 is driven forward, advancing past the coring cannula 20. As the flexible blade 112 advances, it will assume its pre-formed, curved position. Rotation causes the flexible blade 112 to create a semi-circular cut in the tissue. When the flexible transection blade 112 advances past the center of rotation, a complete cut results, releasing the tissue core. The curved blade 112 holds the tissue core inside the cannula 20 until removed from the breast.

The flexible transection blade 112 has a first blade position and a second blade position. The flexible transection blade 112 is in the first blade position while the coring cannula 20 is between the initial and final cannula locations 118, 120. As shown in FIG. 20A, in one embodiment, when the flexible transection blade 112 is in the first blade position it is contained within the coring cannula 20, and thus, not visible. Rotation of the coring cannula 20 in the first direction while the coring cannula 20 is at the final cannula location 120 rotates the flexible transection blade 112 about the axis 24, moving the flexible transection blade 112 from the first blade position to the second blade position (shown in FIG. 22B).

Testing has revealed a few key elements of the invention. First, the most efficient cutting of tissue is accomplished by creating relative motion between cutting surface, i.e., the cutting edge 114, and tissue. Second, the relationship between the cutting edge 114 and the rate of advancement of the length and angle of the cutting edge 114 must result in a cutting surface that is greater in length than the linear advancement per revolution. Further, the rate of advancement per revolution should be optimized to minimize cutting forces. This approach will ensure that a thin, flexible blade 112 will follow the desired cutting path.

Figure 24:
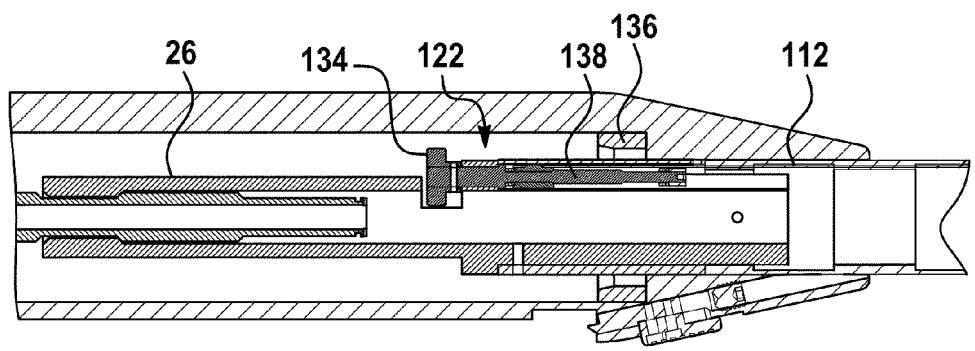
FIG. 24 is a graphical representation of the drivetrain of the device and the flexible transaction blade in the initial position, according to a first embodiment of the present invention.
Figure 25A:
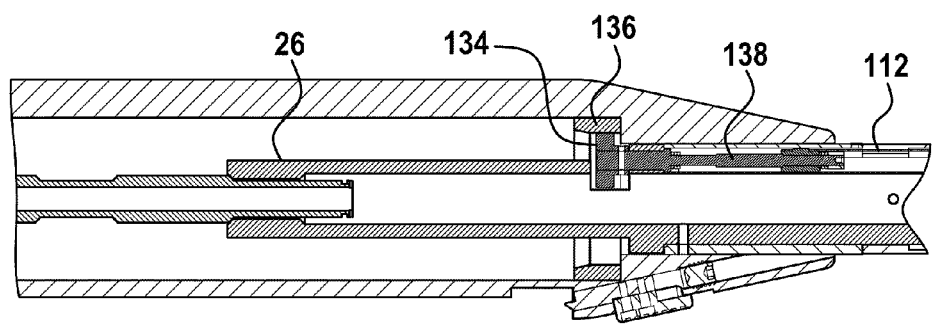
FIG. 25A is a graphical representation of the drivetrain of the device and the flexible transaction blade, of FIG. 24, in the final position.
Figure 25B:
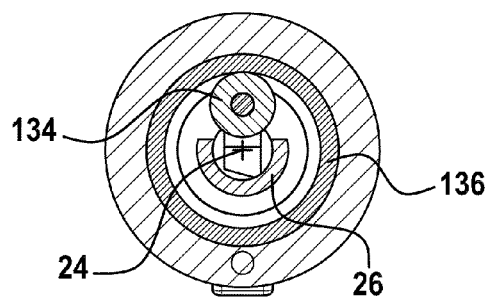
FIG. 25B is a front view of the graphical representation of the drivetrain of the device and the flexible transaction blade, of FIG. 24, in the final position.

With particular reference to FIGS. 24, 25A, and 25B, in one embodiment the mechanism 122 may include a friction wheel transmission 132. The friction wheel transmission 132 includes friction wheel 134 which is force fit over the shaft 26. The shaft 26 is directly coupled to the cannula 20 through a drive ring 20 which is fixed to the housing 14. A drive screw 136 is fixed to the friction wheel 134, which is coupled to the flexible transection blade 112. As the shaft 26 is advanced by the drive assembly 40, the friction wheel 134, and thus the flexible transection blade 116 is also advanced. The friction wheel 134 is force fit over the shaft 26 such that the transmission force may be controlled. The relationship between the friction wheel 134 and the drive ring 136 and/or the relationship between the friction wheel 134 and the shaft 26 can be adjusted so that if the force encountered by the flexible transection blade 112 increases to a certain point, the friction wheel 134 will slip on the shaft 26 preventing further advancement of the blade 112. The blade 112 will continue to rotate until the sample tissue has been cut and the forces reduced. Blade advancement will then automatically resume.

Figure 26:
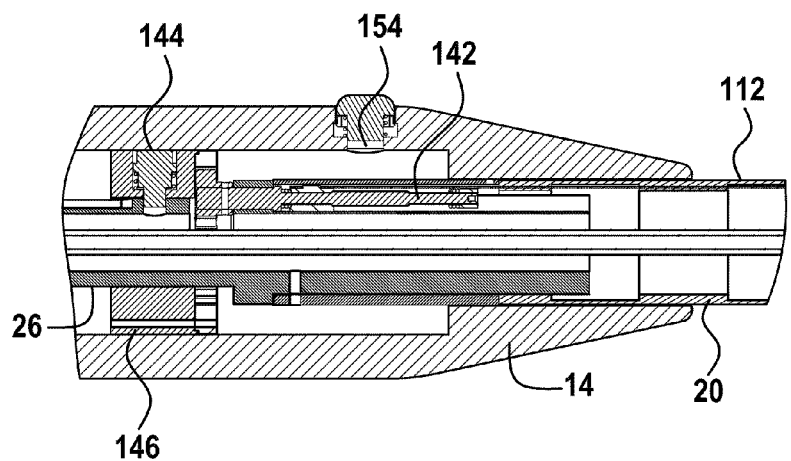
FIG. 26 is a graphical representation of the drivetrain of the device and the flexible transaction blade in the initial position, according to a second embodiment of the present invention.
Figure 27:
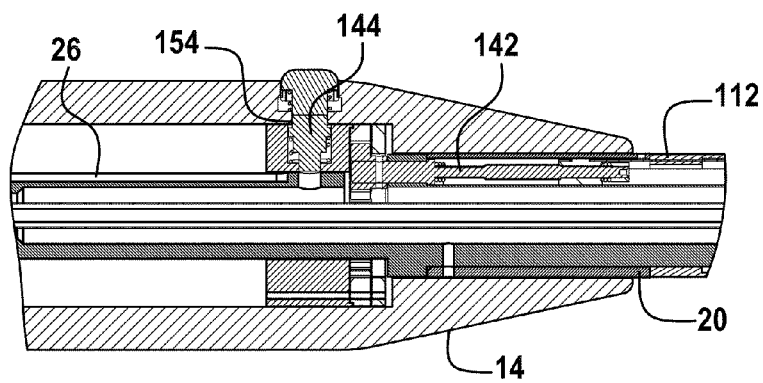
FIG. 27 is a graphical representation of the drivetrain of the device and the flexible transaction blade, of FIG. 24, in the final position.
Figures 28A, 28B:
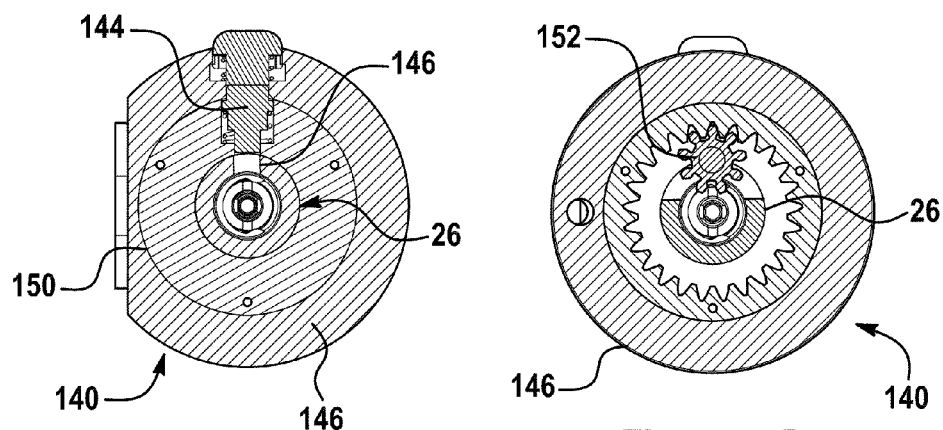
FIG. 28A is a first cut away view of the graphical representation of the drivetrain of the device and the flexible transaction blade, of FIG. 24, in the final position.
FIG. 28B is a second cut away view of the graphical representation of the drivetrain of the device and the flexible transaction blade, of FIG. 24, in the final position.

With particular reference to FIGS. 26, 27, and 28, in another embodiment the mechanism 122 may include a gear drive transmission 140. The gear drive transmission 140 provides continuous drive with maximum power transfer. In one aspect of the present invention, the gears within the gear drive transmission 140 remain meshed but do not rotate during axial advancement of the coring cannula 20. When advancement of the coring cannula 20 is complete, the gear drive transmission 140 automatically engages and begins to drive the flexible transection blade 112.

The gear drive transmission 140 may include a gear housing 146, a ring gear 150, and a drive gear 152. A plunger 144 is slidably coupled to the gear housing 146 and is spring biased in an outward direction. While the coring cannula 20 is between the initial cannula location 118 and the final cannula location 120, plunger 144 is pressed inwardly by the inner wall of the housing 20 such that one end is inserted a receiving slot 148 on the shaft 26. Thus, the gear housing 146 is locked relative to the shaft 26. The shaft gear housing 146 thereby rotates with the shaft 26, and there is no relative motion between the gears 140, 152. When the gear housing 146 reaches a release slot 154 in the housing 14, the spring biased plunger 144 slides into the release slot 154, thereby releasing the shaft 26, the ring gear 150 is fixed relative to the housing 14 and the drive gear 152 rotates with the shaft 26, thereby driving the flexible transection blade 112 forward.

Figure 29:
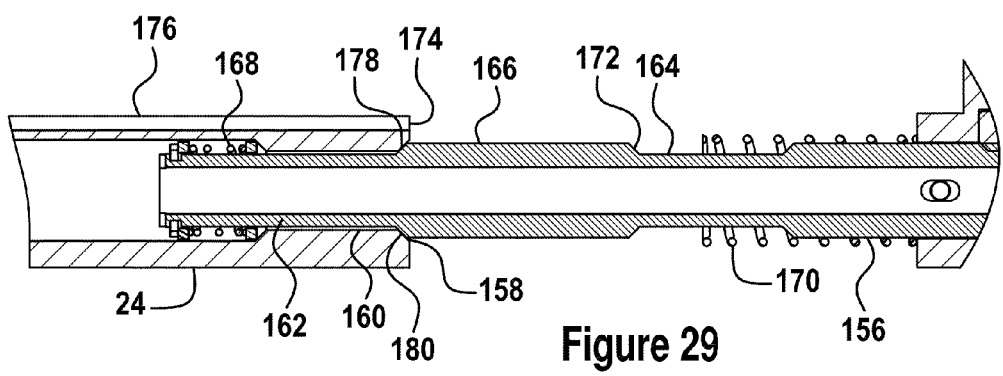
FIG. 29 is a graphical representation of an alternative drivetrain, according to an embodiment of the present invention.

With particular reference to FIG. 29, in still another embodiment a lead screw 156 is used to enable the shaft 26 to advance and rotate, stop advancing but continue rotating and then retract to its original position. The shaft 24 includes an opening 158 leading to a shaft threaded section 160. The lead screw 156 is rotatably fixed to the housing 14 and includes a first end portion 162, a second end portion 164, and a lead screw threaded section 166, which meshes with the shaft threaded section 160.

The shaft 26 is driven forward (to the right in FIG. 29) until the back edge of shaft 174 reaches the front edge of lead screw threads 178. At this position, the shaft 26 will continue to rotate but no longer advances. The shaft threaded portion 160 is supported by shoulder 180. A first spring 168 makes contact with surface 172 exerting a slight backward force on the shaft 26.

When the drive assembly 40 is reversed, the force exerted on surface 172 by the first spring 168 urges re-start of threads between the shaft 26 and the lead screw 156. The shaft 26 will then move backward until the contact surface 176 clears the surface 172. A second spring 170 now provides force to urge restart in the forward direction.

This configuration may also be adopted to drive the flexible transection blade 112.

With particular reference to FIG. 30 in still another embodiment, a drive screw 184 may be used to drive motion of the flexible transection blade 112. A drive gear 182 is fixed to the drive screw 184 which is threadably coupled to the drive dog 186. During forward motion of the coring cannula 20, the drive dog 186 is allowed to slip relative to the drive screw 184. During activation of the flexible transection blade 112, the drive gear 182, and thus, the drive screw 184 rotate. The drive dog 186 has an internal threaded bore (not shown) which is mated with the drive screw 184. As the drive screw 184 rotates, the drive dog 186 advances (or retracts) along the screw 184, thereby advancing the flexible transection blade 112.

With particular reference to FIG. 31, in a further embodiment, a modification is shown. In the illustrated embodiment, the drive dog 186' is fixed to an end of the drive screw 184'. The drive gear 182' has in internal threaded bore (not shown) which is mated with the drive screw 184'. As the drive gear 182' rotates, the drive screw 184' and the drive dog 186' advances or retracts.

As discussed more fully below, the cutting edge 114 of the cutting cannula 20 may be formed by a cannula insert 188 and may have different configurations.

Figure 32A:
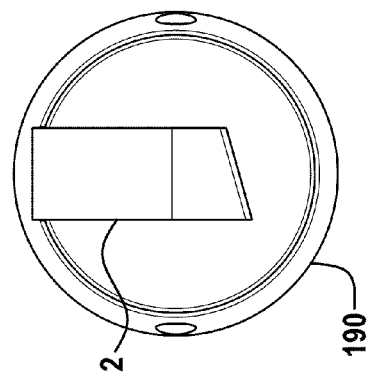
FIG. 32A is a graphical representation of a flexible transection blade and a coring cannula with a circular cutting ring, according to an embodiment of the present invention.
Figure 32B:
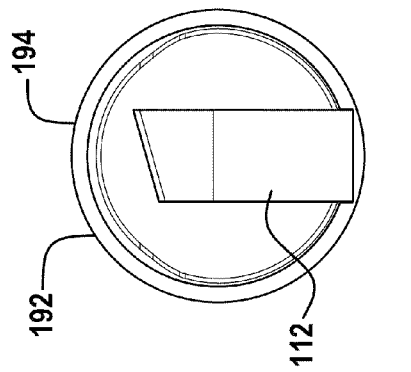
FIG. 32B is a front view of the flexible transection blade and coring cannula of FIG. 32A.

With particular reference to FIGS. 32A and 32B, the cannula insert 188 forms a circular coring blade 190. As shown the flexible transection blade 112 advances past the circular coring blade 190. The flexible blade 112 transects tissue distal to the front edge of cutting ring 190.

Figure 33A:
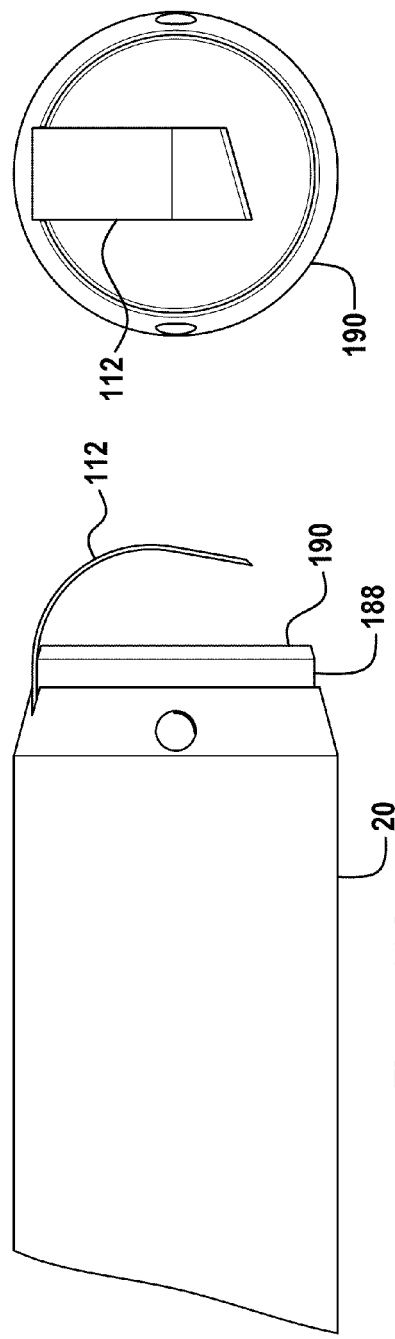
FIG. 33A is a graphical representation of a flexible transection blade and a coring cannula with a partial cutting ring, according to an embodiment of the present invention.
Figure 33B:
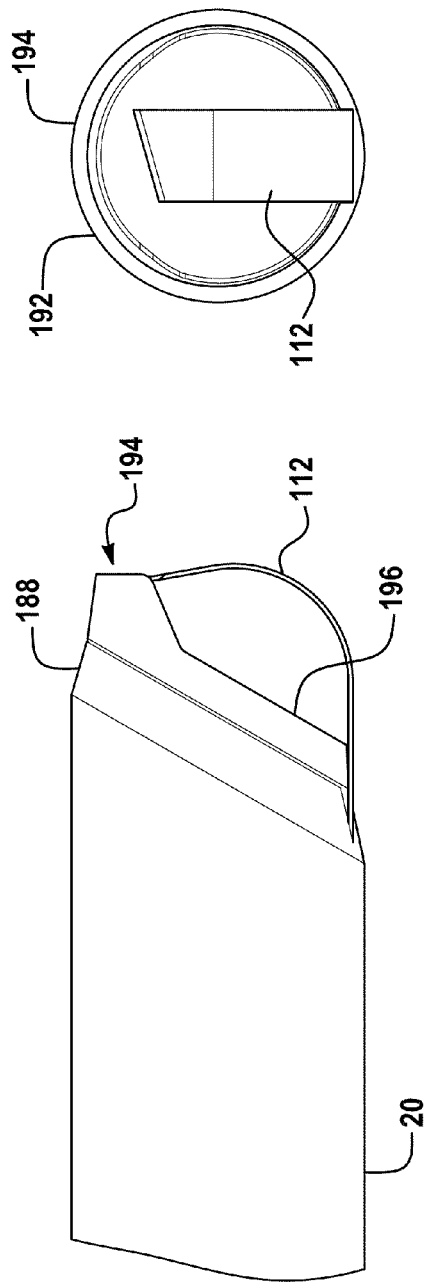
FIG. 33B is a front view of the flexible transection blade and coring cannula of FIG. 33A.

With particular reference to FIGS. 33A and 33B, in another embodiment the cannula insert 188 forms a partial cutting ring 192. The partial cutting ring 192 forms a partial cutting face 194 with an angled edge 196. As the coring cannula 20 rotates, the angled edge 196 cuts through the tissue. As shown, with the partial cutting ring 192, the flexible transection blade 112 does not extend past the furthermost edge of the partial cutting rung 192. Thus, the tissue sample is confined within the cutting ring 192.

Figure 34A:
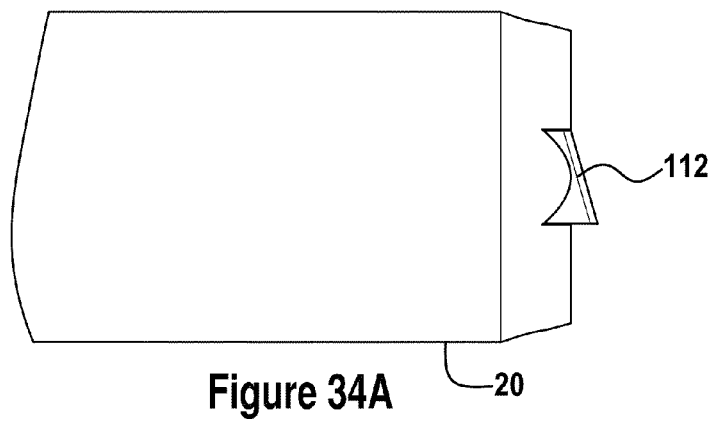
FIG. 34A is a graphical representation of a flexible transection blade which forms the cutting edge of the coring cannula, according to an embodiment of the present invention.
Figure 34B:
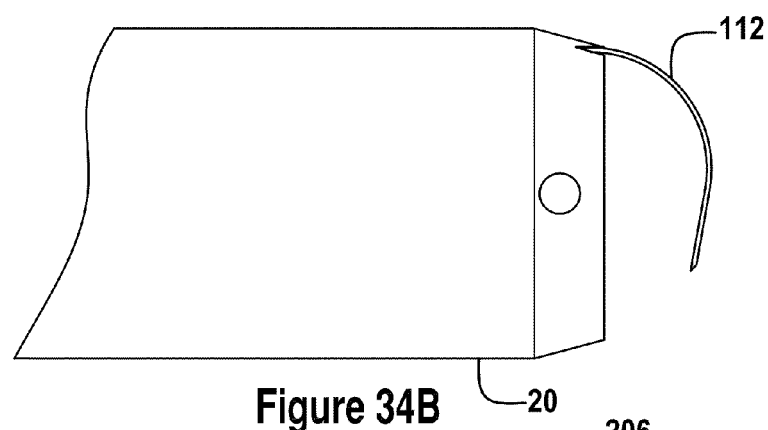
FIG. 34B is a front view of the flexible transection blade and coring cannula of FIG. 34A.

With particular reference to FIGS. 34A and 34B, in still another embodiment, the cutting edge 114 of the flexible transection blade 112 is used to core the sample tissue (FIG. 34A). The flexible transection blade 112 is then advanced to transect tissue (FIG. 34B).

Figure 35:
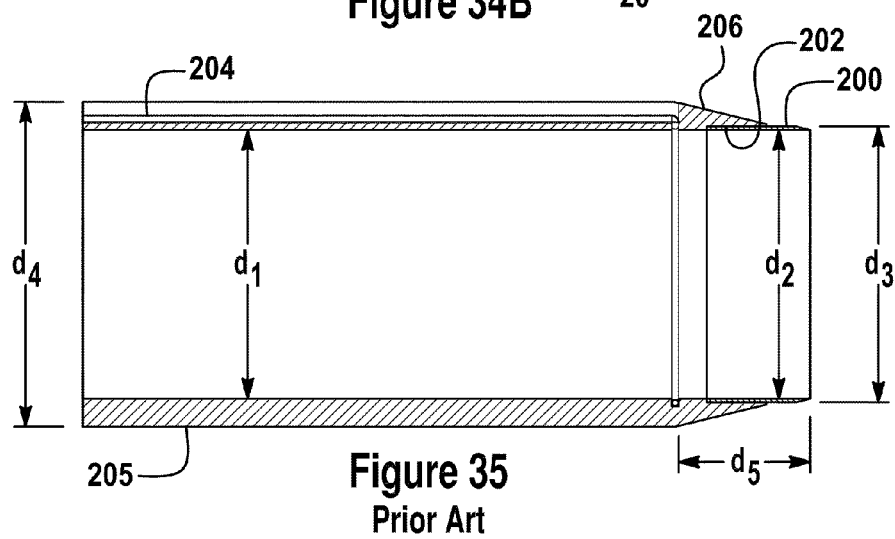
FIG. 35 is a graphical representation of a prior art coring cannula with an internal cutting ring.

With particular reference to FIG. 35, a prior art cutting ring 200 is shown. The prior art cutting ring 200 is nestled within a bore 202 of the distal end of the cutting cannula 20. As shown, the coring cannula 20 has an inner diameter of $d_1$ and the cutting ring 200 has an inner diameter of $d_2$. In the prior art device shown in FIG. 35, $d_1$ is substantially equally to $d_2$. The outer surface of the coring cannula 205 has a ramping surface 206 from the outer dimension of the coring cannula 205 to the distal end of the coring cannula 205. As shown, the outer diameter of the coring cannula $d_4$ is greater than the outer dimension, $d_3$, of the prior art cutting ring 200.

In the prior art cutting ring 200 of FIG. 35, the mechanism for transecting the tissue sample is a garrote wire 204 which transverses the outer wall of the coring cannula 20. At a location near the distal end of the coring cannula 205 the garrote wire 204 forms a right angle and encircles the inner diameter of the coring cannula 20. As shown, this occurs at a substantial distance, $d_5$, from the distal end of the cutting ring 200. This arrangement presents two problems. First, the 90 degree bend in the garrote wire 204 significantly increases the force required to pull the garrote wire and transect the tissue. Second, the large distance, $d_5$, between the garrote wire 204 and the cutting edge of the cutting ring 200, results in a core of tissue, or tissue plug, which is cored by the coring cannula 205, but not transected by the garrote wire. This cored tissue thus remains in the breast.

Figure 36A:
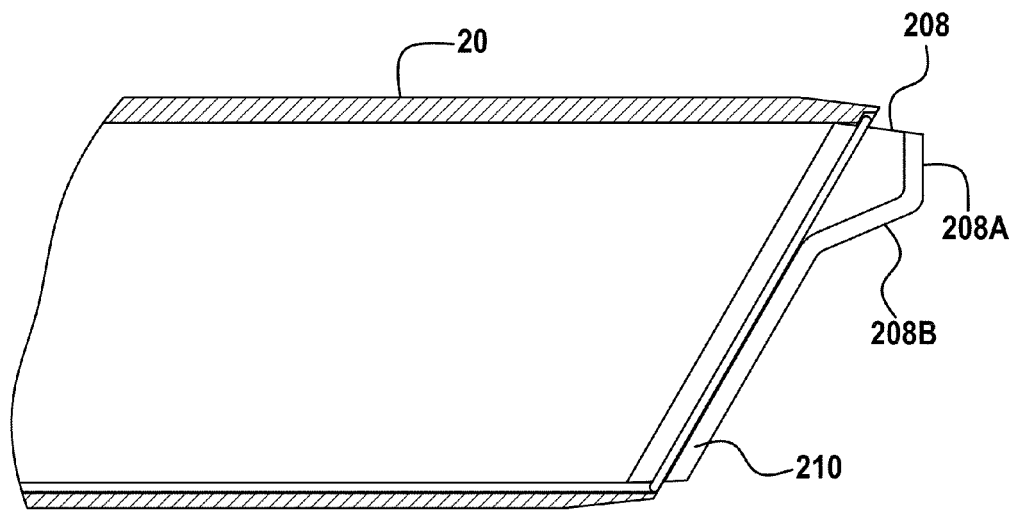
FIG. 36A is a graphical representation of a coring cannula with an angled cutting ring, according to an embodiment of the present invention.
Figure 36B:
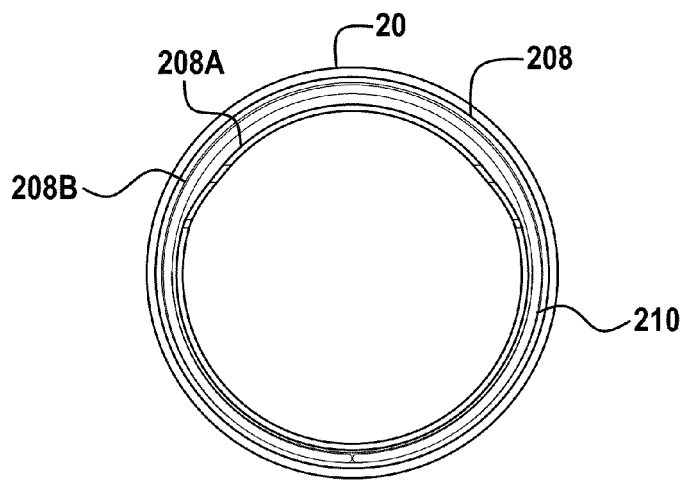
FIG. 36B is a front view of the coring cannula and cutting ring of FIG. 36A.

With particular reference to FIGS. 36A and 36B, in one embodiment a partial cutting ring 208 may be provided. The illustrated partial cutting ring 208 may include a face cutting surface 208A, which has a cutting edge perpendicular to the axis 24, and a side cutting surface 208B. The use of the side cutting surface 208B introduces side cutting. Side cutting is less likely to result in unwanted pushing or movement of tissue. Additionally, the blade angle allows the garrote wire 210 to be installed outside of the coring blade and then clear of the cutting ring when retracting. This also limits the tissue plug problem identified above. Furthermore, the angle in the garrote wire 210 may be increased (as shown), reducing the required transection forces (see FIGS. 37A, 37B, 37C).

Figure 38A:
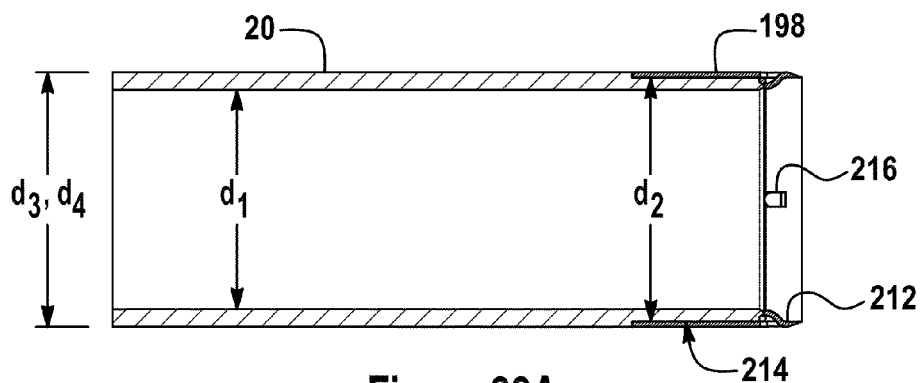
FIG. 38A is a graphical representation of a coring cannula with an external cutting ring, according to an embodiment of the present invention.
Figure 38B:
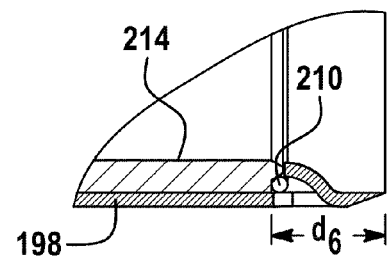
FIG. 38B is a view of a portion of the coring cannula and external cutting ring of FIG. 38A.
Figure 39:
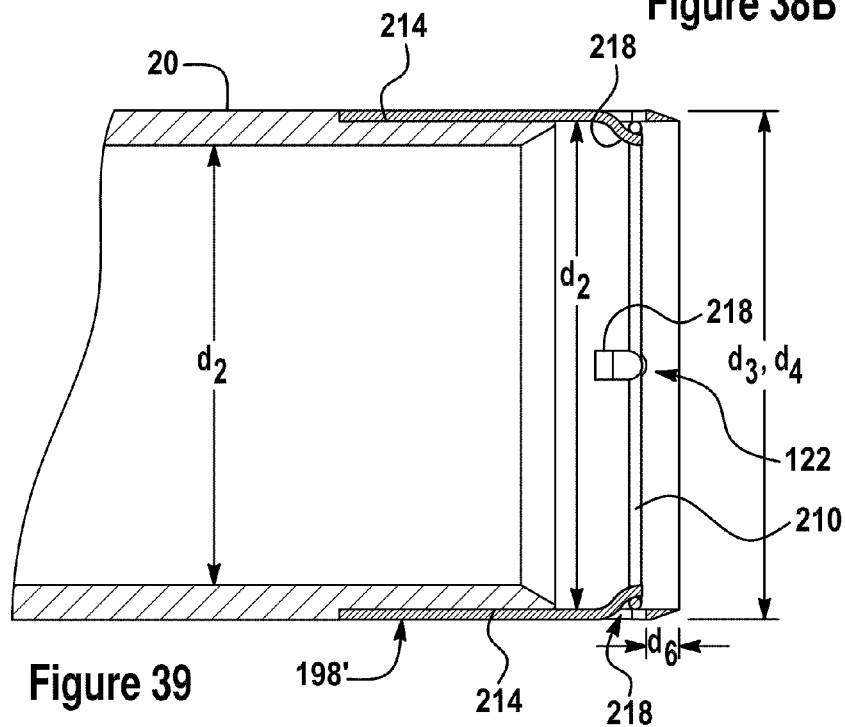
FIG. 39 is a graphical representation of a coring cannula with an external cutting ring, according to an other embodiment of the present invention.

With reference to FIGS. 38A, 38B, and 39 in an other aspect of the present invention, the coring cannula 20 may include an external cutting ring 198. The external cutting ring 198 has an interior bore 212 within an interior diameter, $d_2$. The coring cannula 20 has a reduced diameter portion 214 at its distal end. As shown, the external cutting ring 198 is fitted over the reduced diameter portion of the coring cannula 214.

As shown, the outer diameter ($d_4$) of the coring cannula 20 is substantially equal to the outer diameter of the external cutting ring, $d_3$.

As shown, the transecting mechanism 122 may include a garrote wire 210.

With specific reference to FIGS. 38A and 38B, in one embodiment the garrote wire 210 is removably coupled to the coring cannula 20 by one or more bent tabs 216 formed integrally with the coring cannula 20. The one or more bent tabs 216 may be integrally formed with the coring cannula 20. The mechanism 122 is located at the distal end of the coring cannula 20. The distal end of the coring cannula 20 is within a minimal distance of the distal end of the external cutting ring 198. This minimizes the tissue plug problem discussed above. In one embodiment, the minimal distance is $\leq 0.25$ inches.

With specific reference to FIG. 39, the distal end of the external cutting ring 198 is spaced from the distal end of the coring cannula 20. In the illustrated embodiment, the mechanism 122 is located at the distal end of the external cutting ring 198. The mechanism 122 is within the minimal distance of the distal end of the external cutting ring 198. The garrote wire may be removably held in place by one or more tabs 218 which may be formed integrally with the cutting ring 198.

Figure 41:
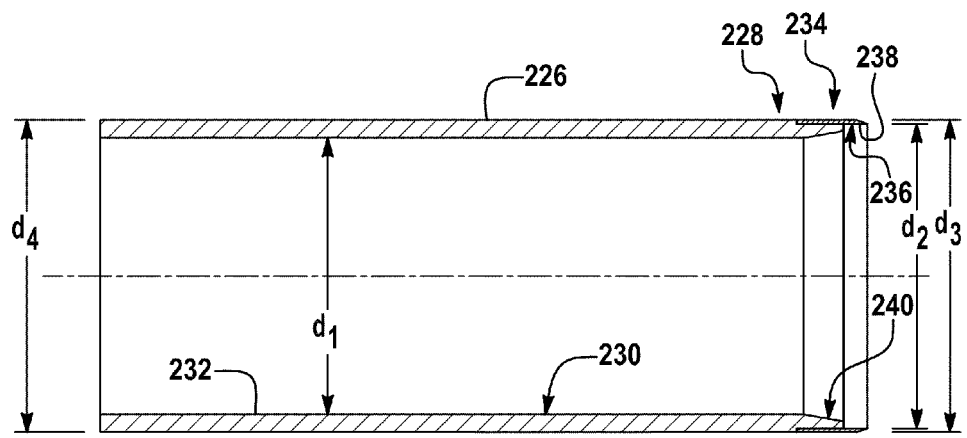
FIG. 41 is a graphical representation of a coring cannula with a cutting ring, according to an embodiment of the present invention.

With particular reference to FIG. 41, in one aspect of the present invention, the coring cannula 20 may be provided with a cutting ring in which the inner diameter of the coring cannula 20 has an inner diameter which is smaller than the inner diameter of the cutting ring. Tissue is flexible, malleable and compressible. With the inner diameter of the coring cannula 20 being smaller than the inner diameter of the cutting ring, the tissue sample is compressed as it enters the coring cannula 20 (behind the cutting ring). Compression of the tissue sample results in better retention of the tissue sample in the cannula 20. Additionally, with the reduced inner diameter of the cannula 20, the outer diameter of the cannula 20 may also be reduced, until it is the equal to or nearly equal to the outer diameter of the cutting ring. This results in (1) a smaller entry incision and (2) reduction of the required coring cutting force.

Figure 40:
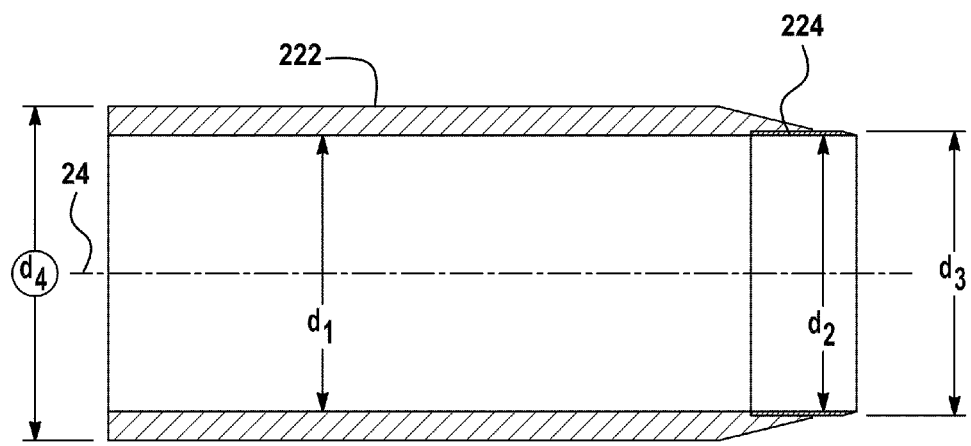
FIG. 40 is a graphical representation of a prior art coring cannula with a cutting ring.

With particular reference to FIG. 40, a prior art cannula 222 is shown. The prior art cannula 222 has a cutting ring 224. The prior art coring cannula 222 has an inner diameter ($d_1$) which is equal to the inner diameter ($d_2$) of the cutting ring 224. Additionally, the outer diameter ($d_4$) of the prior art coring cannula 222 is greater than the outer diameter ($d_3$) of the cutting ring 224.

With particular reference to FIG. 41, a coring cannula 226 according to an embodiment of the present invention is shown. The coring cannula 226 has a distal end 228 and is centered on the axis 24 and is coupled to the housing 14. The coring cannula 226 having an inner surface 230 forming a cannula bore 232. The cannula bore 232 has an inner diameter ($d_1$) and is rotatable about the axis. A cutting ring 234 has an inner surface 236 which forms a cutting ring bore 238 and is located at the distal end of the coring cannula 226. The cutting ring bore 238 has an interior diameter ($d_2$). A tapered wall 240 is coupled between the coring cannula 226 and the cutting ring 234. The tapered wall 240 provides a ramped surface between the inner surface 236 of the cutting ring 234 and the inner surface 236 of the coring cannula 226.

As discussed, the inner diameter, $d_1$, of the cannula bore 232 is less than the inner diameter, $d_2$, of the cutting ring 234. Furthermore, the outer diameter, $d_4$, of the coring cannula 226 is equal to, or only slightly larger than, the outer diameter, $d_3$, of the cutting ring 234.

In one embodiment, the coring cannula 226 and the cutting ring 234 are unitarily formed. In an other embodiment, the coring cannula 226 and the cutting ring 234 are formed separately. In one embodiment (as described above), the coring cannula 226 may have a reduced diameter portion formed at the distal end 228. The cutting ring 234 is an external cutting ring which is fitted over the reduced diameter portion of the coring cannula. The distal end of the cutting ring 234 forms a coring cannula cutting edge 238.

Figure 42A:
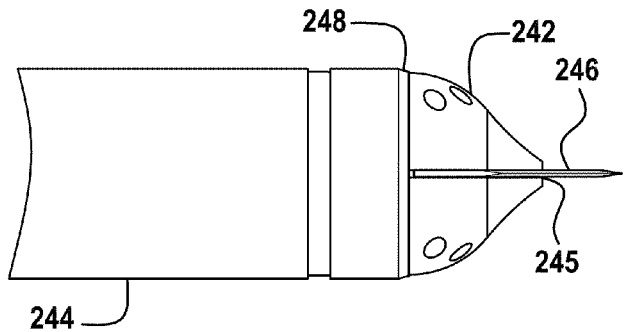
FIG. 42A is a side view of a prior art coring cannula and stylet.
Figure 42B:
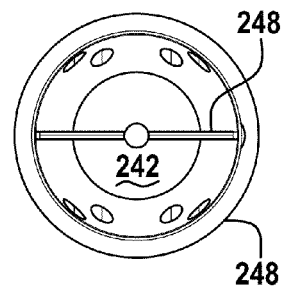
FIG. 42B is a front view of the prior art coring cannula and stylet of FIG. 42A.

With reference to FIGS. 42A, 42B, 43A, 43B, 43C, in another aspect of the present invention a collapsible stylet may be provided (see below). With particular reference to FIGS. 42A and 42B, a prior art stylet 242 is shown. The prior art stylet 242 is contained within the coring cannula 244. The prior art stylet 242 has a slot 243 for the stylet blades 246. The diameter, $d_1$, of the prior art stylet 242 is fixed, and smaller than the diameter, $d_2$, of the cutting edge 248 of the coring cannula 244. Thus, in use, after the stylet 242 has cut into the tissue, the skin may need to be opened further to allow the coring cannula 244 to enter the tissue.

Figure 43A:
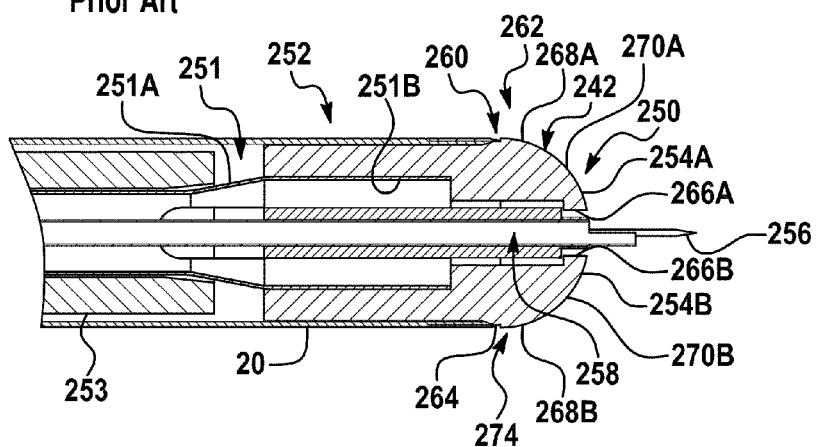
FIG. 43A is a side view of a coring cannula and a collapsible stylet in an initial configuration, according to an embodiment of the present invention.
Figure 43B:
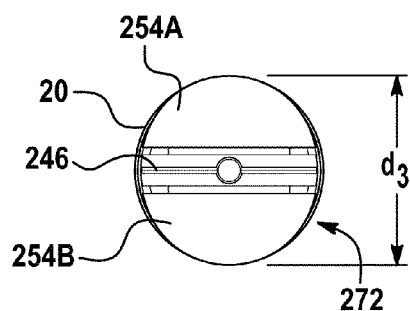
FIG. 43B is a first front view of the coring cannula and stylet of FIG. 43A.
Figure 43C:
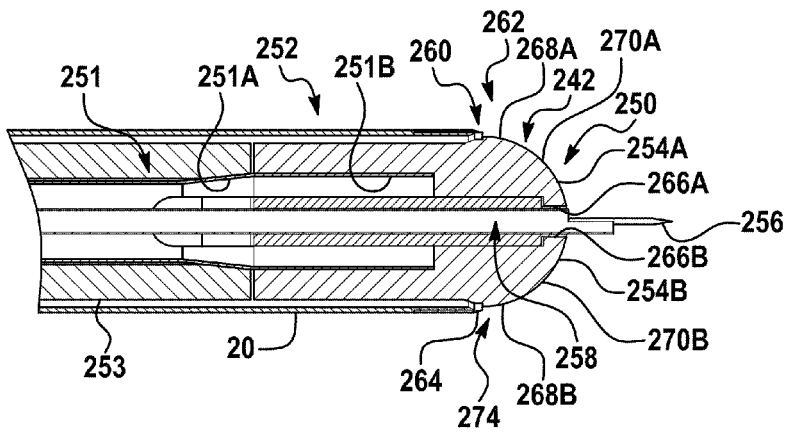
FIG. 43C is a side view of the coring cannula and stylet of FIG. 43A in a contracted configuration.
Figure 43D:
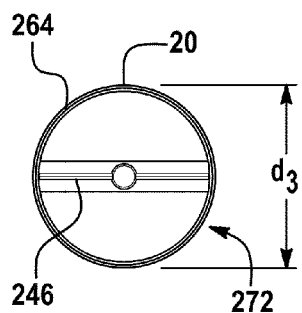
FIG. 43D is a second front view of the coring cannula and stylet of FIG. 43A with the stylet in the contracted configuration.

With particular reference to FIGS. 43A, 43B, and 43C, a collapsible stylet 250 according to one embodiment of the present invention is illustrated. The coring cannula 20 has a distal end 252, a longitudinal axis 24 and is centered on the axis 24 (see above). The collapsible stylet 250 has a tip 254, which contains at least one blade 256, and a central passage 258 and is coupled to the coring cannula 20. The tip 254 has a recess 260 located near a proximal end 262 thereof. The tip 254 is movable between an initial configuration (shown in FIGS. 43A and 43B) and a contracted configuration (shown in FIGS. 43C and 43D). When the tip 254 is in the initial configuration, the cutting edge 264 of the coring cannula 20 is within the recess 260. This allows the coring cannula 20 to enter the incision with the stylet 250, prior to the coring process, without the need to widen or open the incision any further. The tip 250 remains in the initial configuration as the coring cannula 20 is moved from the initial cannula location towards the final cannula location. Once the coring cannula 20 reaches the final cannula location, the tip may be moved into the contracted configuration (FIG. 43C). In the contract configuration, the cutting edge 264 of the coring cannula 20 is exposed when the tip 254 is in the contracted configuration.

In the illustrated embodiment, the tip 254 has a first half portion 254A and a second half portion 254B. As shown in the illustrated embodiment, the first and second half portions 254A, 254B have a semi-circular cross-section (see FIGS. 43B and 43C) and an inner surface 268A, 268B. The inner surface 266A of the first portion 254A faces the inner surface 266B of the second portion 254B. The first and second half portions 254A, 254B have a first part 268A, 268B and a second part 270A, 270B. The second parts 270A, 270B are sloped and curved forming an entry segment 272. The first and second parts 268A, 268B form a linear segment 274. The linear segment 274 has an associated first diameter, ($d_1$), when the tip is in the initial configuration (FIG. 43B). The first diameter associated with the linear segment 274 is greater than or equal to a diameter associated with the cutting edge 248 of the coring cannula 20. Thus, the cutting edge 248 can sit within the recess 260 prior to the coring process (see above).

As shown in FIG. 43C, when the tip 254 is in the contracted configuration the linear segment 274 has a second diameter, ($d_2$). The second diameter is less than diameter associated with the cutting edge 248 of the coring cannula 20. This allows the coring cannula 20 to be rotated and moved forward (over the stylet) to perform the coring process.

In one embodiment, the first and second half portions 254A, 254B are biased towards the initial configuration. In the illustrated embodiment, the collapsible stylet 250 includes a collet tube 251 and a collet closer 253. As shown, the tube 251 includes a ramping portion 251A and a distal end 251B. The distal end 251B is fitted between the first and second half portions 254A, 254B and bias the first and second half portions 254A, 254B into the initial configuration. A collet closer 253 is provided which is movable between a first position (shown in FIG. 43A) and a second position (shown in FIG. 43C). The collet closer 253 acts on the ramping portion 251A of the collet tube 251 to compress the distal end 251B. This allows the first and second half portions 254A, 254B of the collapsible stylet 250 to collapse to the contract position. The collet closer 253 may be movable from the first position to the second position by the user through actuation of a button provided on the housing 14 (not shown).

Figure 44:
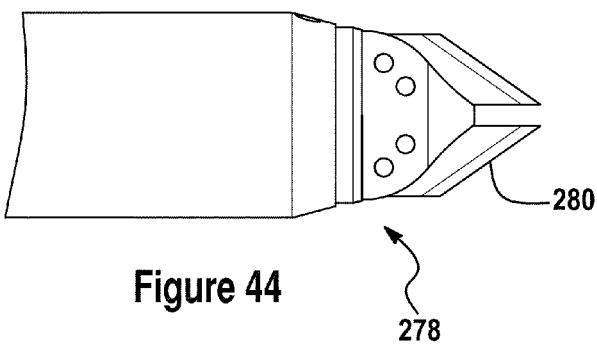
FIG. 44 is a view of a prior art stylet.
Figure 45:
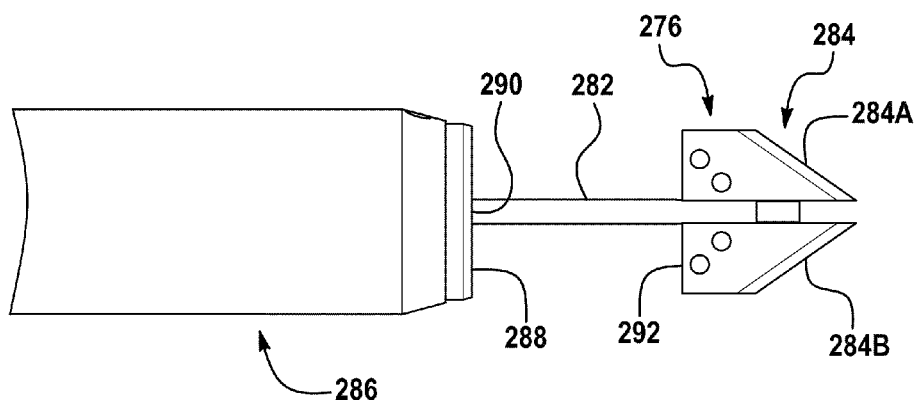
FIG. 45 is a view of a stylet including an independent stylet mechanism, according to an embodiment of the present invention.

With specific reference to FIGS. 44 and 45, in another aspect of the present invention, an independent stylet mechanism 276 is provided. With particular reference to FIG. 44, a prior art stylet 278 is shown. The prior art stylet 278 includes integral cutting blades 280. Since the integral cutting blades 280 are fixed relating to the stylet tip, the distance between the blades 280 and the stylet 278 is fixed at a minimal distance. This increases the chances of inadvertent movement or compression of the tissue, i.e., "snowplowing".

With specific reference to FIG. 45, the independent/retractable stylet mechanism 276 includes a tube 282 and at least one stylet blade 284 affixed to the tube 282. A stylet 286 includes a stylet tip 288 with a central passage 290. The tube 282 is slidably disposed within the central passage 290 of the stylet 286.

In the illustrated embodiment, the stylet mechanism 276 includes first and second blades 284A, 284B.

In one aspect, the tube 282 may include an internal bore 292 for receiving the guide element 52 (see above).

The independent/retractable stylet mechanism 276 is adjustable within/along the central passage 290 of the stylet 286. Thus, the user can adjust the distance between the blades 284 and the stylet tip 288 to reduce the chance of snowplowing occurring.

With reference to FIGS. 46A-46D and 47A-47C, in another aspect of the present invention, a localization needle with an integral locking member 294 is provided. In one embodiment, the localization needle 294 includes a needle portion 296 and a locking member 304. The needle portion 296 having a proximal end 298, a distal end 300 and a channel 302 formed therein.

The locking member 304 is formed integrally with the needle portion 296. As shown, the locking member 304 may be formed at the distal end 300 of the needle portion 296 and has an unlocking configuration (shown in FIG. 46A) and a locking configuration (shown in FIG. 46B).

Figure 46:
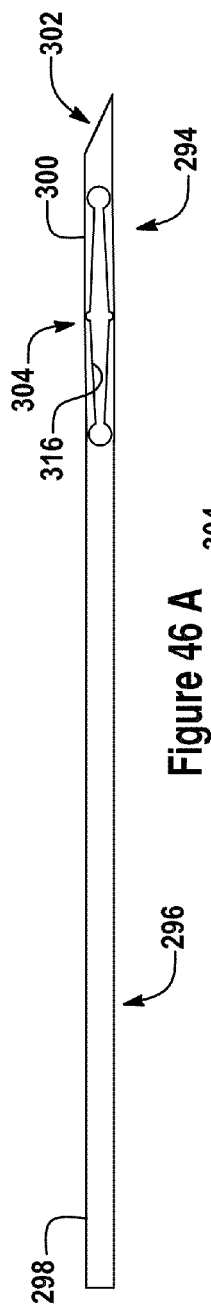
FIG. 46A is a first view of an expanding localization needle, according to an embodiment of the present invention.
FIG. 46B is a second view of the expanding localization needle of FIG. 46A.
FIG. 46C is a view of the expanding localization needle of FIG. 46A with an actuation mechanism, according to a first embodiment of the present invention.
FIG. 46D is a view of the expanding localization needle of FIG. 46A with an actuation mechanism, according to a second embodiment of the present invention.
Figure 46:
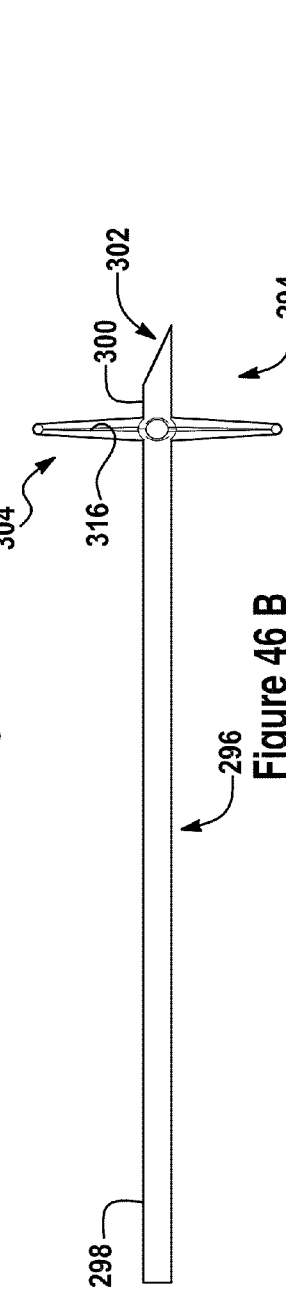
Figure 46:
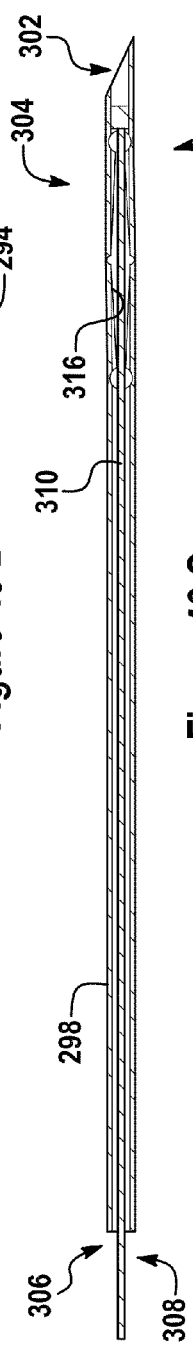
Figure 46:
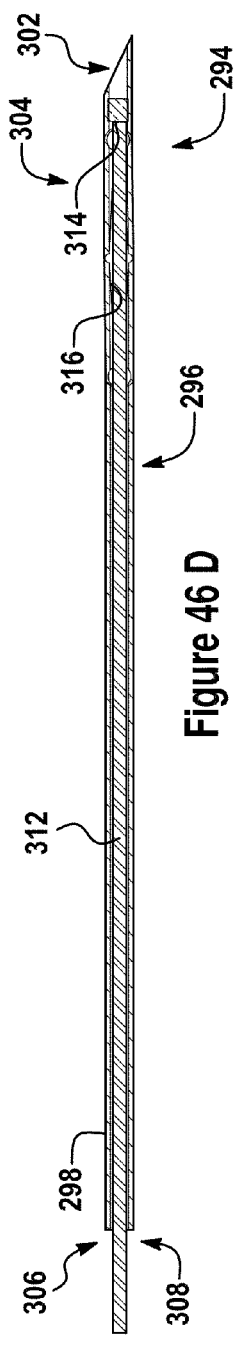

In the illustrated embodiment, in the unlocking configuration, the localization needle 294 is straight, i.e., without bends or kinks. In the locking configuration, bends, or barbs, as shown in FIG. 46B have been introduced into the localization needle 294. These bends, barbs, are introduced into the localization needle 294 after the localization needle 294 has been inserted into the breast, thereby locking the localization needle 294 relative to the target tissue (see above).

In one embodiment, the localization needle 294 includes an actuation device 306. The actuation device 306 is coupled to the distal end 300 and is used to apply a force thereto (see FIG. 46B). The force acts to bring the distal end 300 closer to the proximal end 298. With the proximal end 298 fixed to, for example, the housing 14 of the biopsy device 10, the localization needle 294 collapses at the locking member 304 creating the barbs, or extensions, as shown, thereby controllably moving the locking member from the unlocking configuration to the locking configuration.

In one aspect of the present invention, the actuation device 306 includes a member 308 coupled to an inner surface of the distal end 300 of the needle portion 296.

With particular reference to FIG. 46C, in one embodiment the member 308 may include a wire 310 fixed to the inner diameter of the localization needle 294. The wire 310 may be attached to a lever (not shown) on the housing, or some other suitable mechanism, which pulls the wire 310 back toward the proximal end 298.

In another embodiment, the member 308 is a threaded rod 312 which is received by a threaded receiving member 314 which is coupled to the inner surface of the distal end 300 of the needle portion 296. This arrangement allows the localization needle 294 to be moved back into the unlocking configuration if the placement needs to be corrected.

In another aspect of the present invention, the locking member 304 is formed by at least one pair of opposed slots 316 within the needle portion 296. In one embodiment, the slots 316 may be laser cut from the needle portion 296. As shown in FIGS. 46A-46D, in one embodiment, the slots 316 may have a general rectangular shape with rounded ends. The slots 316 may include one or may directional cutouts 317 which assist in forming the extensions or barbs. The directional cutouts 317 may be triangular shaped.

In another aspect of the present invention the slots 316 may have a general diamond shape, as shown in FIGS. 47A-47C.

Figure 48A:
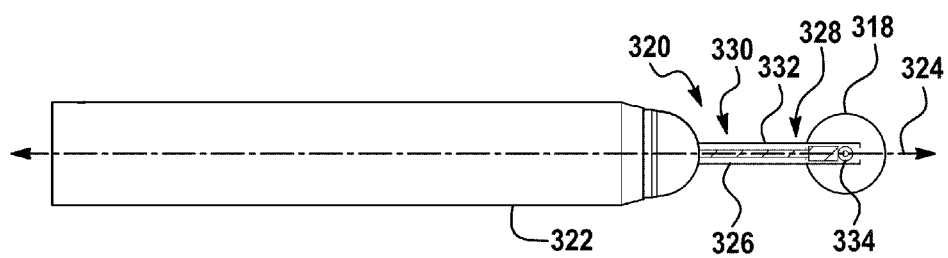
FIG. 48A is a first view of a stylet with a rotating blade, according to an embodiment of the present invention.
Figure 48B:
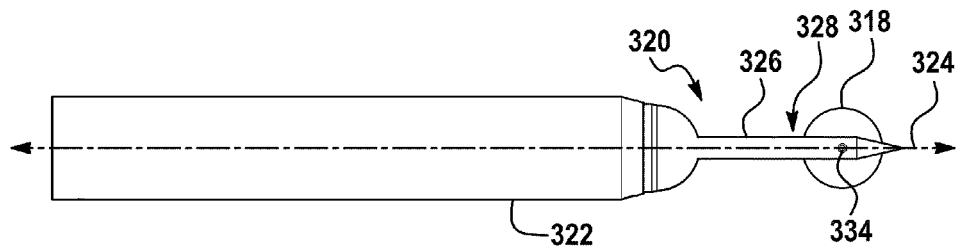
FIG. 48B is a second view of the stylet with the rotating blade of FIG. 48A.
Figure 49:
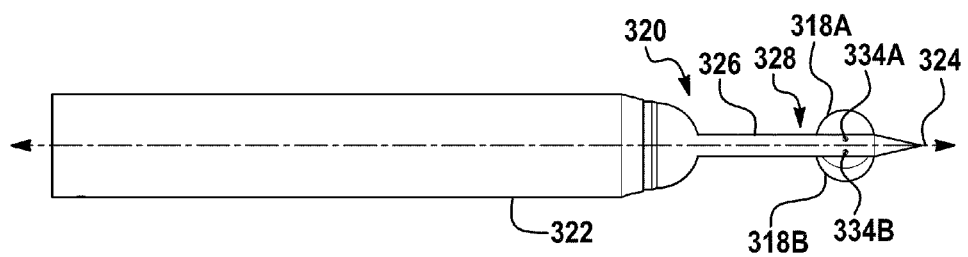
FIG. 49 is an illustration of a stylet with multiple rotating blades, according to an embodiment of the present invention.

With particular reference to FIGS. 48A, 48B, and 49, in another aspect of the present invention, one or more rotating circular blades 318, 318A, 318B may be used. The use of the rotating circular blades 318, 318A, 318B improves the efficiency of the stylet and reduces the risk of compression and/or tearing of the tissue as the stylet in pushed into the breast.

The rotating circular blade(s) 318, 318A, 318B may be powered (see below) or may rotating freely. The rotation of the blade (s) 318, 318A, 318B whether from an external source or as a result of friction between the blade 318, 318A, 318B and the tissue, creates relative motion therebetween.

With particular reference to FIG. 48A, in one embodiment a stylet 320 is provided with a single rotating circular blade 318. The stylet 320 is coupled to a coring cannula 322. The coring cannula 322 has a longitudinal axis 324 and is centered on the axis 324. The stylet 320 is coupled to the coring cannula 322. The stylet 320 includes a stylet tube 326. The rotating circular blade 318 is rotatably coupled to a distal end 328 of the stylet tube 326.

With particular reference to FIG. 48B, in another embodiment, the rotating circular blade 318 is not mechanically driven, but is allowed to freely rotate. As the device 10 is advanced into the tissue, force exerted by the tissue will tend to rotate the circular blade 318, eliminating the tendency to push/tear tissue and improving cutting efficiency.

In both embodiments, the singular rotating circular blade 318 is mounted on its center point 334. As shown, the center point 334 is centered over the stylet tube 326.

The rotating circular blade 318 defines a first plane which is parallel to the axis 324. The axis defines a second plane. The first and second planes intersect at a right angle. The center point 334 of the rotating circular blade 318 is located on both the first and second planes.

A blade drive mechanism 330 is coupled to the rotating circular blade 318 for controllably rotating the circular blade 318. In one embodiment, the blade drive mechanism 330 may include a motor (not shown) and drive cable 332. Alternatively, the blade drive mechanism 330 may include a rod and gearing system (not shown).

With particular reference to FIG. 49, the stylet 320 may include a pair of offset blades 318A, 318B. The second blade 318B defines a third plane which is parallel to the first plane. As shown in FIG. 39, the center 334A, 334B of the blades 318A, 318B are offset a predetermined distance. The first and second blades 318A, 318B may be mechanically driven or may be allowed to rotate freely.

Returning to FIGS. 2A-2D, 5A and 5B, in another aspect of the present invention the biopsy device 10 includes at least one retractable stylet blade 336. The at least one retractable stylet blade 336 is part of a stylet blade mechanism 338. The stylet blade mechanism 338 may include first and second retractable blades 336A, 336B, as shown.

The stylet blade mechanism 338 is coupled to the coring cannula 20 via the stylet tip 30. In one embodiment, the stylet blade mechanism 338 includes the stylet tube 36. The at least one retractable stylet blade 336 is fixed to the stylet tube 36. The stylet tube 36 is slidably disposed within the stylet housing 38. The central passage 34 is formed by the stylet tube 36.

The stylet blade mechanism 338 is movable between a cutting position and a retracted position. In the cutting position, the at least one stylet blade is located a distance in front of the stylet tip 30 (as shown). In the retracted position, the at least one stylet blade 336 is located within the stylet tip 30.

In one embodiment, the stylet blade mechanism 338 may be manually moved from the retracted position to the cutting position. In one embodiment, the stylet blade mechanism 338 is spring biased towards the cutting position.

As discussed above, the biopsy device 10 may further comprise a guide portion 108 formed at the end of the stylet tube 30. The guide portion 108 extends past an opening of the stylet tube 30. The guide portion 108 having an interior curved surface 340. The interior curved surface 340 assists in guiding the end of the guide element 52 into the central passageway 108.

It should be noted that the stylet blade mechanism 338 and the retractable stylet blades 336 may be used with either integrated localization needle or the independent needle (see above). With respect to FIGS. 5A and 5B, the stylet blade mechanism 338 is used with the independent needle handle assembly 18'. As discussed above, the independent needle handle assembly 18' is inserted into the breast, the guide element 52 is extended outside of the needle 54 and the locking member 62 is affixed to the target tissue. Once the locking member 62 is locked into the target tissue, the guide element 52 is removed from the needle 54. The guide element 52 is then inserted into central passageway 108.

With the guide element 52 within the central passageway 108 and the stylet blade mechanism 338 in the cutting position, the biopsy device 10 is slid up the guide element 52, the stylet blades 336 cutting the tissue and allowing the device 10 to reach the target tissue. Once the target tissue is reached, the stylet blade mechanism 338 can be retracted such that the blade(s) 336 are contained within the tip 30. The coring cannula 20 can then be advanced over the target tissue.

With reference to FIGS. 50A, 50B, 50C, 50D, 51A and 51B, in still another aspect of the present invention, a garrote wire 210 is used to transect the tissue sample.

The prior art devices, which employ a garrote wire, use a linear pull "trigger" system to activate the garrote wire. A limitation of the design is the travel required to fully pull the garrote wire. This limitation becomes an issue for larger cannula sizes. As the cannula diameter increases, the length of garrote wire required to transect tissue increases resulting in an increase in required travel. The travel length is limited by the overall length of the device. Continuing to increase the device length is not a viable option.

As discussed below, the breast biopsy device 10 may include a trigger mechanism 342 which includes a trigger 344 (shown diagrammatically in FIGS. 50A-51B). The trigger 344 is generally pulled backward to pull garrote wire 210 backward, thereby transecting the tissue sample within the coring cannula 20.

Figure 50A:
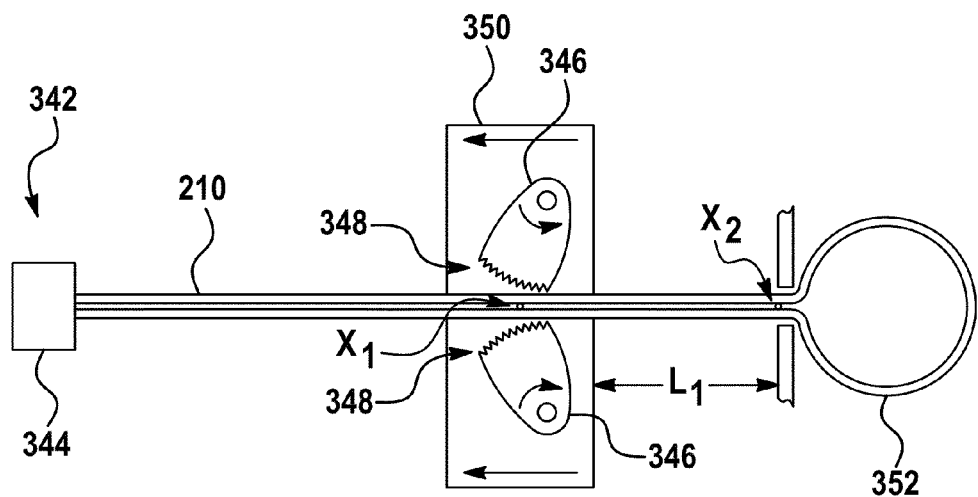
FIG. 50A is a graphical representation of a portion of a breast biopsy device with a garrote wire and a trigger mechanism includes a pair of cleats.
Figure 50B:
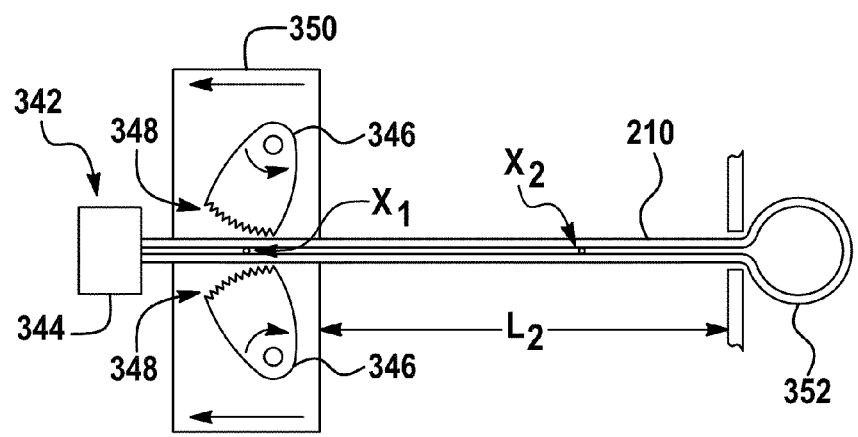
FIG. 50B is a second graphical representation of the breast biopsy device of FIG. 5A.

As shown in FIG. 50A, the breast biopsy device 10 includes a pair of rotatable cleats 346 which are coupled to the housing 14 (through a trigger body 350) and are rotatable between a first cleat position (shown in FIG. 50A) and a second cleat position (shown in FIG. 50B). As shown, in one embodiment, the rotatable cleats 346 include a plurality of teeth 348 which grip the garrote wire 210. The cleats 346 are coupled to the trigger mechanism 342 and when the trigger mechanism 342 is actuated, i.e., pulled backward relative to the housing 14. Friction causes the cleats 346 to rotate, thereby engaging the teeth 348 into the garrote wire 210. Then, as the trigger mechanism 342 is pulled backward, the cleats 346 move therewith, pulling the garrote wire 210 as well.

With specific reference to FIG. 50A, when the garrote wire 210 is in a first position, the wire 210 forms a loop 352 which is external to the coring cannula 20. After the coring cannula 20 is extended and surrounds the sample tissue, the trigger mechanism 342 is used to complete separate the sample tissue from the breast.

In one embodiment, a single actuation of the trigger mechanism 342, e.g., a single pull of the trigger 342, moves the garrote wire 210 from the first wire position to a second wire position in which the garrote wire 210 is within the coring cannula 20 (and the sample completely separated from the breast).

In another embodiment, multiple actuations of the trigger mechanism 342, or multiple pulls of the trigger 344, are required. In the illustrated embodiment, two pulls of the trigger 344 are required. Each pull of the trigger 344, moving the garrote wire a distance defined by the distance between $X_1$ and $X_2$.

FIG. 50A shows the garrote wire 210 in an initial position with the loop 352 in its largest configuration. FIG. 50B shows the garrote wire 210 in an intermediate location, after the first pull of the trigger 344 (the trigger 344 and trigger body 350 are shown at full travel).

Figure 50C:
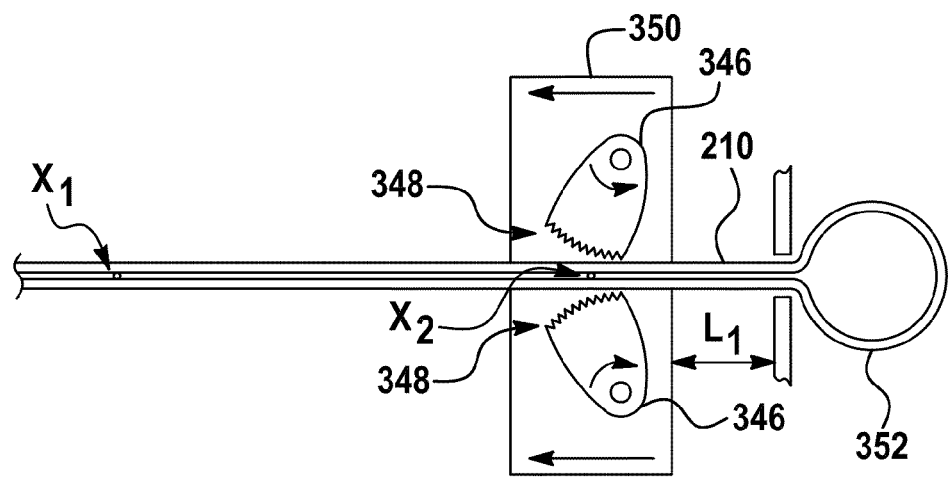
FIG. 50C is a third graphical representation of the breast biopsy device of FIG. 50A.

FIG. 50C shows the garrote wire 210 at the intermediate location, with the trigger body 350 returned to the initial position. In one aspect, the trigger body 350 is spring biased back to the initial position. In another aspect, the trigger body 350 may be manually moved back to the initial position.

Figure 50D:
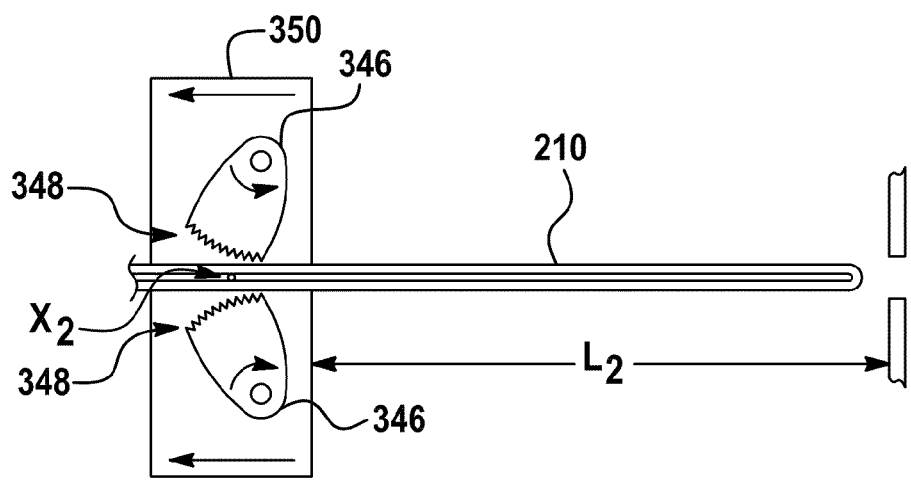
FIG. 50D is a fourth graphical representation of the breast biopsy device of FIG. 50A.

FIG. 50D shows the garrote wire 210 at the final location, fully actuated and within the coring cannula 20. At this point, the sample is completely severed from the breast.

This improvement to the linear pull system will enable the use of larger cannula sizes to provide for multiple pulls of the trigger 344 on the garrote wire 210. Multiple pulls can be accomplished using the breakaway cleat system. The cleat system works as follows: When the trigger 348 is pulled, cleats 346 with separated edges or teeth 348 grip the garrote wire 210, allow the trigger 344 to pull the wire 219 the full length of travel. At the end of travel, the trigger 344 is pushed forward back to the start position. When the trigger 344 is moved in this direction, the cleat 346 (cam) disengages the wire so that the trigger 344 slides forward without affecting the wire 210. As the trigger 344 is pulled back, the cleats 346 re-engage the wire 210, pulling it to further transect tissue. This process is repeated until transection is completed.

Figure 51A:
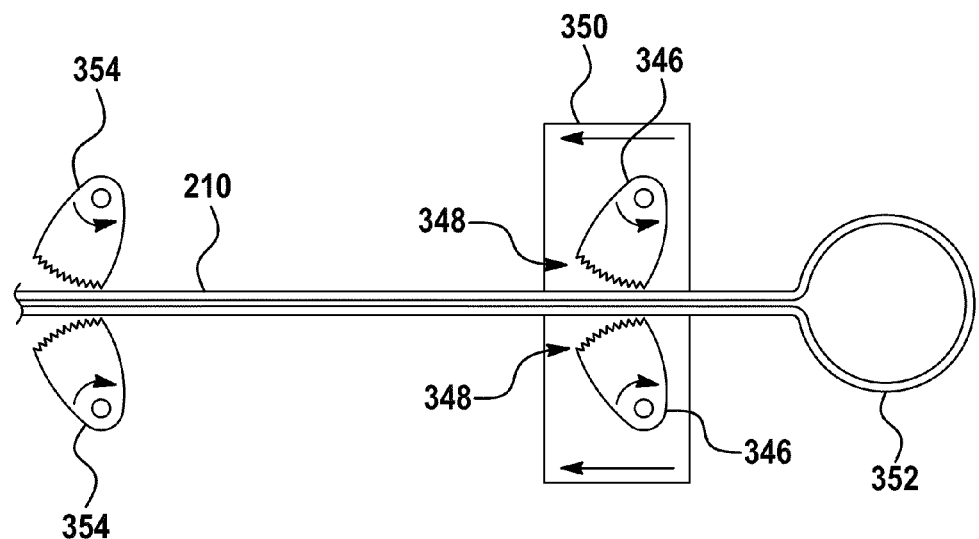
FIG. 51A is a graphical representation of another embodiment of the trigger mechanism of FIG. 50A.

With reference to FIG. 51A in a further embodiment, a second pair rotatable cleats 354 may be fixed directly to the device 10, e.g., directly to the housing 14. The second pair of rotatable cleats 354 are not fixed to the trigger body 350. The second pair of cleats 354 prevented undesirable forward motion of the garrote wire 210.

Figure 51B:
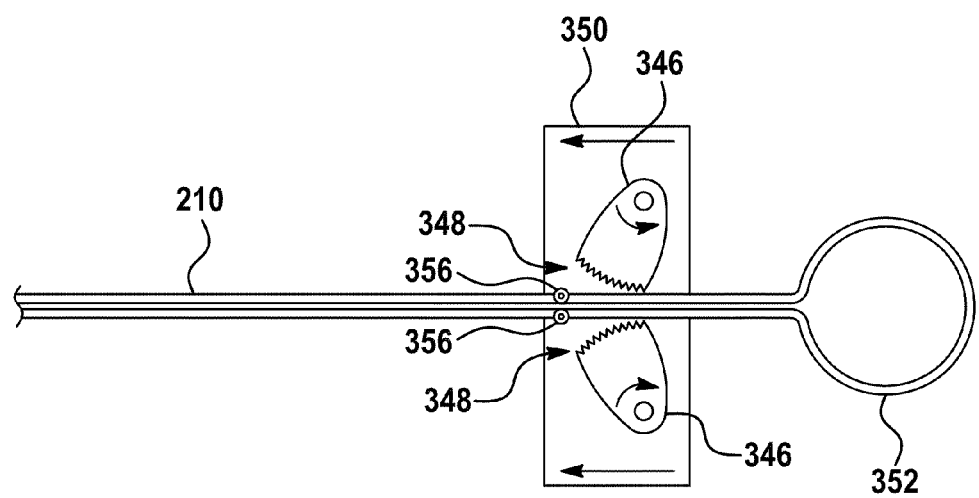
FIG. 51B is a graphical representation of a further embodiment of the trigger mechanism of FIG. 50A.
Figure 52A:
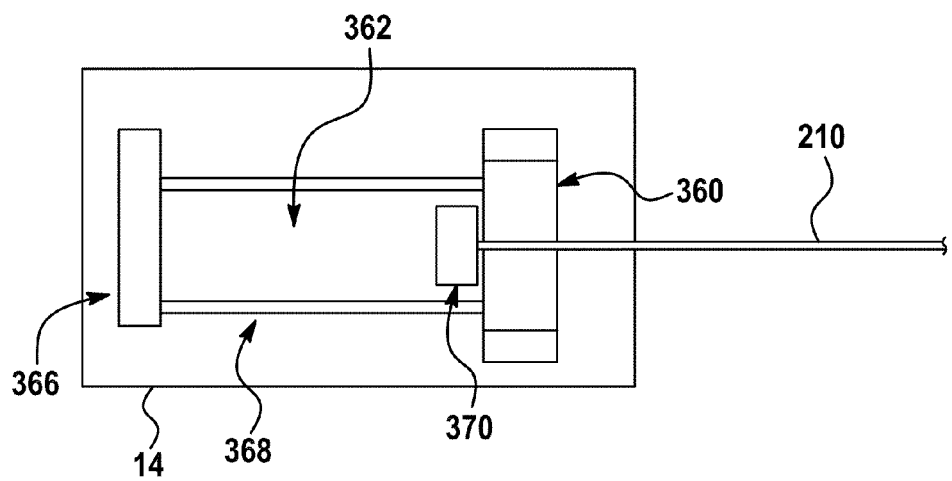
FIG. 52A is a top view of a graphical representation of a top view of a breast biopsy device having a rotatable trigger, according to an embodiment of the present invention.
Figure 52B:
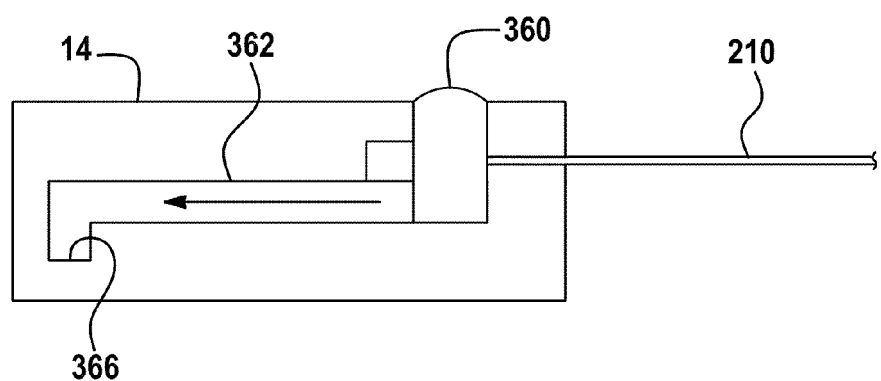
FIG. 52B is a side view of the breast biopsy device of FIG. 52A.
Figure 52C:
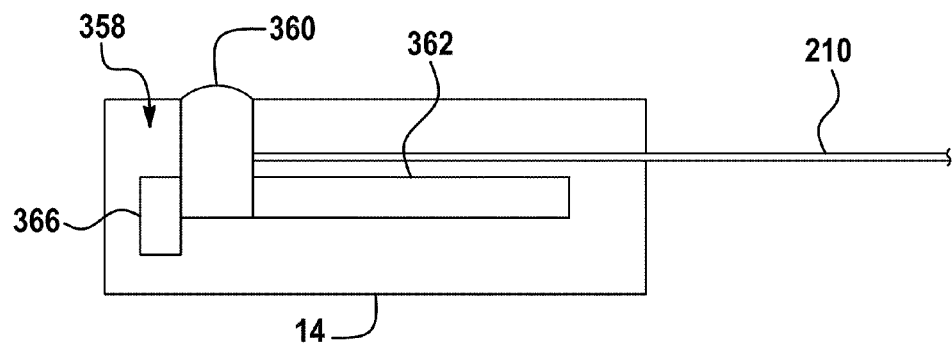
FIG. 52C is a second view of the breast biopsy device of FIG. 52A.
Figure 52D:
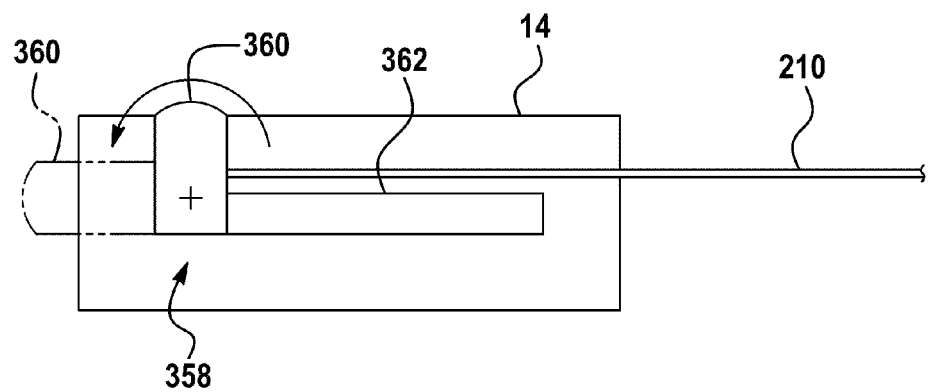
FIG. 52D is a third view of the breast biopsy device of FIG. 52A.

With reference to FIG. 51B in an other embodiment, the garrote wire 210 may have a number of beads 356 fixed thereto (crimped or welded thereon) to assist in grabbing of the wire by the cleats 346, 354.

As discussed above, the prior art utilizes a linear pull trigger system, in which the trigger is pulled straight back to actuate the garrote wire. The trigger rides in a track and is supported by guide rods to maintain the desired linear pull. When the trigger is pulled back it engages a support ring attached to the garrote wire. This support ring moves backward with the trigger, pulling the garrote wire across the cannula, transecting the core of tissue at the distal end. However, there are a significant number of cases which encounter "tough" breast tissue. When tough tissue is encountered, transection force increases significantly, at times resulting in incomplete transection. The user cannot provide enough input force to fully actuate the trigger system. Occurrences of this problem increases as cannula diameter increases.

Constriction and transection of breast tissue by the garrote wire can best be described by separating it into two phases. Phase 1 includes 0% to 70-95% constriction of the tissue by the garrote wire. The 70-95% range is dependent on cannula size and tissue density. The requirements of Phase 1 are long travel and low/medium input force. The current linear pull system works well during Phase 1. Phase 2 covers up to the final 30% of tissue constriction and eventual transection. The requirements of Phase 2 are limited travel with potentially high input forces required. The linear pull system does not always meet these requirements.

With reference to FIGS. 52A, 52B, 52C, and 52D, in another aspect of the present invention, the garrote wire 210 actuation by a trigger mechanism 358. The trigger mechanism 358 is coupled to the housing 14 and the garrote wire 210 (via support ring 370). In the illustrated embodiment, the trigger mechanism 358 includes a trigger 360 slidably mounted in a trigger channel 362 in the housing 14. In the illustrated embodiment the trigger channel 362 is formed by a linear support track 368 within the housing 14. The trigger 360 is movable from a first trigger position (shown in FIGS. 52A and 52B) to an intermediate trigger position (shown in FIG. 52C) within the trigger channel 362.

The garrote wire 210 is coupled directly to the trigger 360. In response to the trigger 360 being moved from the first trigger position to the intermediate trigger position, the garrote wire is moved from the first wire position to an intermediate wire position. In the illustrated embodiment, the triggers 360 drops into a cam channel 366 once it reaches the intermediate trigger position.

Once the trigger 360 reaches the intermediate trigger position it can move no further within the trigger channel 362. The trigger 360 is further rotatably movable about a trigger axis 364 from the intermediate trigger position to a second trigger position (shown dotted lines in FIG. 52D). In response to movement of the trigger 360 to the second trigger position, the garrote wire 210 is moved from the intermediate wire position to the second wire position in response thereto.

The addition of a rotational cam mechanism, i.e., the rotatable trigger 360, to the trigger mechanism 358 will address Phase 2. The rotational cam provides a mechanical advantage to the user allowing greater input force with limited travel. The concept described here is a "hybrid" system, using the linear pull system for the first 70-95% wire travel and then switching to the rotational cam system for the final phase of transection.

In use, the user will pull the trigger 360 along the linear track. At an optimized position, the trigger 360 will reach the end of the trigger channel and engage the cam activation system. In this position the trigger will no longer translate, but will now rotate so that the input force is transferred through the cam to the support ring 370.

Any modifications and variations of the present invention are possible in light of the above teachings. The invention may be practiced otherwise than as specifically described within the scope of the appended claims.

What is claimed is:

1. A biopsy device, comprising:
a housing;
a coring cannula having a distal end, a longitudinal axis and being centered on the axis and coupled to the housing, the coring cannula being rotatable about the axis, the distal end of the coring cannula having a cutting edge;
a stylet having a tip containing at least one blade and a central passage and being coupled to the coring cannula, the tip having a recess located at a proximal end thereof and movable between an initial configuration and a contracted configuration, the cutting edge of the coring cannula being within the recess when the tip is in the initial configuration, the tip being movable into the contracted configuration, the cutting edge of the coring cannula being exposed when the tip is in the contracted configuration.

2. A biopsy device, as set forth in claim 1, wherein tip has a first half portion and a second half portion, the first and second half portions having a semi-circular cross-section and an inner surface, the inner surface of the first portion facing the inner surface of the second portion.

3. biopsy device, as set forth in claim 2, the first and second half portions having a first part and a second part, the second parts being sloped and curved forming an entry segment.

4. A biopsy device, as set forth in claim 3, the first and second parts forming a linear segment, the linear segment having an associated first diameter when the tip is in the initial configuration.

5. A biopsy device, as set forth in claim 4, wherein the first diameter associated with the linear segment is greater than or equal to a diameter associated with the cutting edge of the coring cannula.

6. A biopsy device, as set forth in claim 5, wherein the linear segment has an associated second diameter when the tip is in the contracted configuration.

7. A biopsy device, as set forth in claim 6, wherein the second diameter is less than diameter associated with the cutting edge of the coring cannula.

8. A biopsy devices, as set forth in claim 2, wherein first and second half portions are biased towards the initial configuration.

9. A biopsy device, as set forth in claim 1, further comprising a localization needle being slidably disposed within the central passage of the stylet.

10. A biopsy device, as set forth in claim 9, the central passage being formed by a stylet tube, the central passage including an opening.

11. A biopsy device, as set forth in claim 10, wherein stylet tube includes a guide portion which extends past the opening.

12. A biopsy devices, as set forth in claim 9, further comprising:

a drive mechanism for rotating the cannula and moving the cannula in a direction parallel to the longitudinal axis of the cannula;

a guide element having a first end and a second end and being slidably disposed within the channel of the localization needle, the guide element being movable from a first position to a second position within the localization needle; and a locking member formed at the second end of the guide element, the locking member having an unlocking configuration and a locking configuration, the locking member being in the unlocking configuration and contained within the localization needle when the guide wire is in the first position, the locking member being in the locking configuration and being outside the localization needle when the guide element is in the second position.

13. A biopsy device, as set forth in claim 12, including a needle assembly including an actuator and a holder, the localization needle being removably coupled to the actuator and being slidable through an aperture in the holder.

14. A biopsy device, as set forth in claim 13, wherein the holder is separate from the housing.

15. A biopsy device, as set forth in claim 13, the biopsy device being a handheld device and including a handle, the handle being removably coupled to the housing.

16. A biopsy device, as set forth in claim 1, the coring cannula being movable along the axis from an initial cannula location towards a final cannula location in response to rotation of the coring cannula about the axis in a first direction, the tip being in the initial configuration as the coring cannula is moved from the initial cannula location towards the final cannula location.

17. A biopsy device, comprising:

a housing;

a coring cannula having a distal end, a longitudinal axis and being centered on the axis and coupled to the housing, the coring cannula rotatable about the axis, the distal end of the coring cannula having a cutting edge;

a stylet having a tip containing at least one blade and a central passage and being coupled to the coring cannula, the tip having a recess located at a proximal end thereof and being movable between an initial configuration and a contracted configuration, the cutting edge of the coring cannula being within the recess when the tip is in the initial configuration, the tip being movable into the contracted configuration, the cutting edge of the coring cannula being exposed when the tip is in the contracted configuration;

a localization needle slidably disposed within the central passage;

a motor assembly coupled to the coring cannula for controllably rotating the cannula;

a variable speed circuit electrically coupled to the motor assembly;

a forward/reverse switch electrically coupled to the variable speed circuit for controlling the direction of movement of the cannula; and, a speed control trigger electrically coupled to the variable speed circuit, the variable speed circuit for responsively controlling the speed and rotation of the cannula as a function of the forward/reverse switch and actuation of the speed control trigger.

18. A biopsy device, as set forth in claim 17, the coring cannula being movable along the axis from an initial cannula location towards a final cannula location in response to rotation of the coring cannula about the axis in a first direction, the tip being in the initial configuration as the coring cannula is moved from the initial cannula location towards the final cannula location, the motor assembly for simultaneously advancing the cannula as the cannula is rotated.

* * * * *